(12) United States Patent
Fischer et al.

(10) Patent No.: US 8,846,946 B2
(45) Date of Patent: Sep. 30, 2014

(54) GERMINAL ALKOXY/ALKYLSPIROCYCLIC SUBSTITUTED TETRAMATE DERIVATIVES

(71) Applicant: Bayer CropScience AG, Monheim (DE)

(72) Inventors: Reiner Fischer, Monheim (DE); Stefan Lehr, Liederbach (DE); Jan Dittgen, Frankfurt (DE); Dieter Feucht, Eschborn (DE); Ulrich Görgens, Ratingen (DE); Isolde Häuser-Hahn, Leverkusen (DE); Christopher Hugh Rosinger, Hofheim (DE); Arnd Voerste, Köln (DE); Eva-Maria Franken, Lyons (FR); Olga Malsam, Rösrath (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/755,611

(22) Filed: Jan. 31, 2013

(65) Prior Publication Data

US 2014/0213795 A1    Jul. 31, 2014

Related U.S. Application Data

(62) Division of application No. 12/591,456, filed on Nov. 19, 2009, now Pat. No. 8,389,443.

(30) Foreign Application Priority Data

Dec. 2, 2008    (EP) .................................... 08170489

(51) Int. Cl.
| | |
|---|---|
| C07D 235/02 | (2006.01) |
| C07C 233/52 | (2006.01) |
| C07C 233/16 | (2006.01) |
| C07C 229/48 | (2006.01) |
| C07C 233/23 | (2006.01) |

(52) U.S. Cl.
CPC ............ C07D 235/02 (2013.01); C07C 229/48 (2013.01); C07C 233/23 (2013.01); C07C 233/52 (2013.01)
USPC ........... 548/301.4; 560/43; 562/458; 562/507

(58) Field of Classification Search
None
See application file for complete search history.

(56) References Cited

U.S. PATENT DOCUMENTS

| | | |
|---|---|---|
| 2,842,476 A | 7/1958 | Schreiber |
| 4,623,727 A | 11/1986 | Hübele |
| 4,639,266 A | 1/1987 | Heubach et al. |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,944,790 A | 7/1990 | Moser et al. |
| 4,985,063 A | 1/1991 | Fischer et al. |
| 5,013,659 A | 5/1991 | Bedbrook et al. |
| 5,045,560 A | 9/1991 | Fischer et al. |
| 5,116,836 A | 5/1992 | Fischer et al. |
| 5,215,570 A | 6/1993 | Burckhardt et al. |
| 5,225,434 A | 7/1993 | Bertram et al. |
| 5,258,527 A | 11/1993 | Krauskopf et al. |
| 5,314,863 A | 5/1994 | Löher et al. |
| 5,380,852 A | 1/1995 | Schütze et al. |
| 5,401,700 A | 3/1995 | Sohn et al. |
| 5,462,912 A | 10/1995 | Hioki et al. |
| 5,462,913 A | 10/1995 | Fischer et al. |
| 5,500,367 A | 3/1996 | Hain et al. |
| 5,504,057 A | 4/1996 | Fischer et al. |
| 5,508,436 A | 4/1996 | Fischer et al. |
| 5,516,750 A | 5/1996 | Willms et al. |
| 5,538,937 A | 7/1996 | Hasebe et al. |
| 5,567,671 A | 10/1996 | Fischer et al. |

(Continued)

FOREIGN PATENT DOCUMENTS

| | | |
|---|---|---|
| CA | 1 162 071 | 2/1984 |
| CA | 2 077 896 | 9/1991 |

(Continued)

OTHER PUBLICATIONS

Baur, P., et al., "Polydisperse Ethoxylated Fatty Alcohol Surfactants as Accelerators of Cuticular Penetration. 1. Effects of Ethoxy Chain Length and the Size of the Penetrants," *Pesticide Science* 51:131-152, John Wiley & Sons, GB (1997).

(Continued)

*Primary Examiner* — Alicia L Otton
(74) *Attorney, Agent, or Firm* — Sterne, Kessler, Goldstein & Fox P.L.L.C.

(57) ABSTRACT

The invention relates to novel compounds of the formula (I)

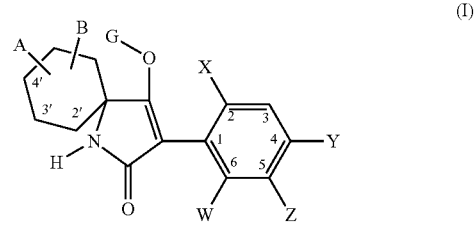

(I)

in which W, X, Y, Z, A, B and G have the meanings given above, to a plurality of processes and intermediates for their preparation, and to their use as pesticides and/or herbicides. The invention also provides selective herbicidal compositions comprising, firstly, geminally alkoxy/alkylspirocyclically substituted tetramic acid derivatives and, secondly, a crop plant compatibility-improving compound. The invention furthermore relates to the boosting of the action of crop protection compositions comprising compounds of the formula (I) through the addition of ammonium salts or phosphonium salts and optionally penetrants.

5 Claims, No Drawings

(56) References Cited

U.S. PATENT DOCUMENTS

| | | | |
|---|---|---|---|
| 5,589,469 A | 12/1996 | Fischer et al. |
| 5,622,917 A | 4/1997 | Fischer et al. |
| 5,683,965 A | 11/1997 | Bachmann et al. |
| 5,689,046 A | 11/1997 | Schröder et al. |
| 5,700,758 A | 12/1997 | Rösch et al. |
| 5,705,476 A | 1/1998 | Hoffarth |
| 5,739,079 A | 4/1998 | Holdgrun et al. |
| 5,792,755 A | 8/1998 | Sagenmuller et al. |
| 5,811,374 A | 9/1998 | Bertram et al. |
| 5,830,826 A | 11/1998 | Fischer et al. |
| 5,972,839 A | 10/1999 | Ziemer et al. |
| 5,994,274 A | 11/1999 | Fischer et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |
| 6,251,827 B1 | 6/2001 | Ziemer et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,589,976 B1 | 7/2003 | Fischer et al. |
| 6,602,823 B1 | 8/2003 | Röchling et al. |
| 6,608,211 B1 | 8/2003 | Hagemann et al. |
| 6,645,914 B1 | 11/2003 | Woznica et al. |
| 6,861,391 B1 | 3/2005 | Fischer et al. |
| 6,894,005 B1 | 5/2005 | Maetzke et al. |
| 7,569,517 B2 | 8/2009 | Fischer et al. |
| 7,718,186 B2 | 5/2010 | Fischer et al. |
| 7,727,933 B2 | 6/2010 | Fischer et al. |
| 8,389,443 B2 | 3/2013 | Fischer et al. |
| 2003/0216260 A1 | 11/2003 | Ruther et al. |
| 2003/0224939 A1 | 12/2003 | Miles |
| 2004/0224844 A1 | 11/2004 | Bickers et al. |
| 2005/0009880 A1 | 1/2005 | Cottrell et al. |
| 2005/0037922 A1 | 2/2005 | Bickers et al. |
| 2005/0049145 A1 | 3/2005 | Bickers et al. |
| 2005/0054535 A1 | 3/2005 | Fischer et al. |
| 2005/0090399 A1 | 4/2005 | Friedmann et al. |
| 2005/0096386 A1 | 5/2005 | Cottrell et al. |
| 2005/0256000 A1 | 11/2005 | Schaper et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0015825 A1 | 1/2007 | Fischer et al. |
| 2007/0032539 A1 | 2/2007 | Himmler |
| 2007/0112035 A1 | 5/2007 | Jeschke et al. |
| 2007/0129252 A1 | 6/2007 | Fischer et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0254949 A1 | 11/2007 | Bretschneider et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0027114 A1 | 1/2008 | Funke et al. |
| 2008/0167188 A1 | 7/2008 | Fischer et al. |
| 2008/0220973 A1 | 9/2008 | Fischer et al. |
| 2008/0287435 A1 | 11/2008 | Fischer et al. |
| 2008/0305955 A1 | 12/2008 | Bretschneider et al. |
| 2008/0318776 A1 | 12/2008 | Fischer et al. |
| 2009/0012152 A1 | 1/2009 | Fischer et al. |
| 2009/0029858 A1 | 1/2009 | Fischer et al. |
| 2009/0209513 A1 | 8/2009 | Fischer et al. |
| 2009/0215624 A1 | 8/2009 | Fischer et al. |
| 2009/0227563 A1 | 9/2009 | Fischer et al. |
| 2009/0239906 A1 | 9/2009 | Fischer et al. |
| 2009/0281157 A1 | 11/2009 | Fischer et al. |
| 2009/0298828 A1 | 12/2009 | Fischer et al. |
| 2009/0305891 A1 | 12/2009 | Fischer et al. |
| 2010/0004127 A1 | 1/2010 | Fischer et al. |
| 2010/0009850 A1 | 1/2010 | Fischer et al. |
| 2010/0048661 A1 | 2/2010 | Fischer et al. |
| 2010/0113437 A1 | 5/2010 | Fischer et al. |
| 2010/0130578 A1 | 5/2010 | Fischer et al. |
| 2010/0137233 A1 | 6/2010 | Fischer et al. |

FOREIGN PATENT DOCUMENTS

| | | |
|---|---|---|
| CA | 2 671 179 A1 | 6/2008 |
| DE | 10 2005 059 892 A1 | 6/2007 |
| EP | 0 036 106 A2 | 9/1981 |
| EP | 0 086 750 A2 | 8/1983 |
| EP | 0 094 349 A2 | 11/1983 |
| EP | 0 131 624 B1 | 1/1985 |
| EP | 0 142 924 A2 | 5/1985 |
| EP | 0 174 562 A2 | 3/1986 |
| EP | 0 191 736 A2 | 8/1986 |
| EP | 0 193 259 A1 | 9/1986 |
| EP | 0 221 044 A1 | 5/1987 |
| EP | 0 242 236 A1 | 10/1987 |
| EP | 0 242 246 B1 | 10/1987 |
| EP | 0 257 993 A2 | 3/1988 |
| EP | 0 262 399 A2 | 4/1988 |
| EP | 0 268 554 A2 | 5/1988 |
| EP | 0 269 806 A1 | 6/1988 |
| EP | 0 305 398 B1 | 3/1989 |
| EP | 0 309 862 A1 | 4/1989 |
| EP | 0 333 131 A1 | 9/1989 |
| EP | 0 346 620 A1 | 12/1989 |
| EP | 0 355 599 A1 | 2/1990 |
| EP | 0 365 484 A1 | 4/1990 |
| EP | 0 377 893 A2 | 7/1990 |
| EP | 0 415 211 A2 | 3/1991 |
| EP | 0 442 073 A2 | 8/1991 |
| EP | 0 442 077 A2 | 8/1991 |
| EP | 0 453 086 A2 | 10/1991 |
| EP | 0 456 063 A2 | 11/1991 |
| EP | 0 464 461 A2 | 1/1992 |
| EP | 0 492 366 A2 | 7/1992 |
| EP | 0 521 334 A1 | 1/1993 |
| EP | 0 582 198 A2 | 2/1994 |
| EP | 0 595 130 A1 | 5/1994 |
| EP | 0 596 298 A2 | 5/1994 |
| EP | 0 613 884 A2 | 9/1994 |
| EP | 0 613 885 A2 | 9/1994 |
| EP | 0 664 081 A2 | 7/1995 |
| EP | 0 668 267 A1 | 8/1995 |
| EP | 0 681 865 A2 | 11/1995 |
| FR | 2 600 494 A1 | 12/1987 |
| GB | 2 266 888 A | 11/1993 |
| JP | 60-87254 A | 5/1985 |
| JP | 2000-53670 A | 2/2000 |
| JP | 2002-205984 A | 7/2002 |
| WO | WO 84/02919 | 8/1984 |
| WO | WO 91/07874 A1 | 6/1991 |
| WO | WO 91/08202 A1 | 6/1991 |
| WO | WO 91/13972 A1 | 9/1991 |
| WO | WO 91/19806 A1 | 12/1991 |
| WO | WO 92/00377 A1 | 1/1992 |
| WO | WO 92/11376 A1 | 7/1992 |
| WO | WO 92/14827 A1 | 9/1992 |
| WO | WO 92/16108 A1 | 10/1992 |
| WO | WO 95/01971 A1 | 1/1995 |
| WO | WO 95/07897 A1 | 3/1995 |
| WO | WO 95/17817 A1 | 7/1995 |
| WO | WO 95/20572 A1 | 8/1995 |
| WO | WO 95/26954 A1 | 10/1995 |
| WO | WO 96/25395 A1 | 8/1996 |
| WO | WO 96/35664 A1 | 11/1996 |
| WO | WO 97/01535 A1 | 1/1997 |
| WO | WO 97/02243 A1 | 1/1997 |
| WO | WO 97/36868 A1 | 10/1997 |
| WO | WO 97/43275 A2 | 11/1997 |
| WO | WO 97/45016 A1 | 12/1997 |
| WO | WO 98/05638 A2 | 2/1998 |
| WO | WO 98/06721 A1 | 2/1998 |
| WO | WO 98/13361 A1 | 4/1998 |
| WO | WO 98/25928 A1 | 6/1998 |

(56) References Cited

FOREIGN PATENT DOCUMENTS

| | | |
|---|---|---|
| WO | WO 98/27049 A1 | 6/1998 |
| WO | WO 98/35553 A1 | 8/1998 |
| WO | WO 98/38856 A1 | 9/1998 |
| WO | WO 99/00020 A1 | 1/1999 |
| WO | WO 99/16744 A1 | 4/1999 |
| WO | WO 99/16748 A1 | 4/1999 |
| WO | WO 99/24437 A1 | 5/1999 |
| WO | WO 99/43649 A1 | 9/1999 |
| WO | WO 99/48869 A1 | 9/1999 |
| WO | WO 99/55673 A1 | 11/1999 |
| WO | WO 00/35278 A1 | 6/2000 |
| WO | WO 01/17972 A2 | 3/2001 |
| WO | WO 01/23354 A2 | 4/2001 |
| WO | WO 01/74770 A1 | 10/2001 |
| WO | WO 02/34048 A1 | 5/2002 |
| WO | WO 03/013249 A1 | 2/2003 |
| WO | WO 03/059065 A1 | 7/2003 |
| WO | WO 03/062244 A1 | 7/2003 |
| WO | WO 2004/007448 A1 | 1/2004 |
| WO | WO 2004/024688 A1 | 3/2004 |
| WO | WO 2004/065366 A1 | 8/2004 |
| WO | WO 2004/080962 A1 | 9/2004 |
| WO | WO 2004/084631 A1 | 10/2004 |
| WO | WO 2004/111042 A1 | 12/2004 |
| WO | WO 2005/015994 A1 | 2/2005 |
| WO | WO 2005/016001 A1 | 2/2005 |
| WO | WO 2005/044791 A2 | 5/2005 |
| WO | WO 2005/044796 A1 | 5/2005 |
| WO | WO 2005/048710 A1 | 6/2005 |
| WO | WO 2005/049569 A1 | 6/2005 |
| WO | WO 2005/066125 A1 | 7/2005 |
| WO | WO 2005/092897 A2 | 10/2005 |
| WO | WO 2005/112630 A1 | 12/2005 |
| WO | WO 2006/000355 A1 | 1/2006 |
| WO | WO 2006/024411 A2 | 3/2006 |
| WO | WO 2006/029799 A1 | 3/2006 |
| WO | WO 2006/056281 A1 | 6/2006 |
| WO | WO 2006/056282 A1 | 6/2006 |
| WO | WO 2006/089633 A2 | 8/2006 |
| WO | WO 2007/023719 A1 | 3/2007 |
| WO | WO 2007/023764 A1 | 3/2007 |
| WO | WO 2007/048545 A2 | 5/2007 |
| WO | WO 2007/068427 A2 | 6/2007 |
| WO | WO 2007/068428 A2 | 6/2007 |
| WO | WO 2007/073856 A2 | 7/2007 |
| WO | WO 2007/096058 A1 | 8/2007 |
| WO | WO 2007/121868 A1 | 11/2007 |
| WO | WO 2007/140881 A1 | 12/2007 |
| WO | WO 2008/006513 A1 | 1/2008 |
| WO | WO 2008/006515 A1 | 1/2008 |
| WO | WO 2008/006516 A1 | 1/2008 |
| WO | WO 2008/067873 A1 | 6/2008 |
| WO | WO 2008/067910 A8 | 6/2008 |
| WO | WO 2008/067911 A1 | 6/2008 |
| WO | WO 2008/138551 A2 | 11/2008 |
| WO | WO 2009/000443 A8 | 12/2008 |
| WO | WO 2009/003597 A1 | 1/2009 |
| WO | WO 2009/015801 A1 | 2/2009 |
| WO | WO 2009/039975 A1 | 4/2009 |
| WO | WO 2009/049851 A1 | 4/2009 |
| ZA | 985601 | 1/1999 |

OTHER PUBLICATIONS

Bhattacharya, B., "Isoquinoline Derivatives: Part XVIII—Formation of I-Alkyl-(or alkaryl or aryl)-3-methyl-7-chloro-(or 5-chloro)-isoquinolines," *Indian Journal of Chemistry* 6:341-345, National Institute of Science Communication and Information Resources, IN (1968).

Braun, H.-P., et al., "The general mitochondrial processing peptidase from potato is an integral part of cytochrome $c$ reductase of the respiratory chain," *The EMBO Journal* 11(9):3219-3227, Oxford University Press, UK (1992).

Christou, P., "Transformation technology," *Trends in Plant Science* 1(12):423-431, Elsevier Science Ltd., UK (1996).

Compagnon, P. and Miocque, M., "Addition Des Réactifs Nucléophiles Sur La Triple Liaison Nitrile," *Ann. Chim.* 5:11-22, Wiley Interscience, FR (1970).

Edward, J.T., and Jitrangsri, C., "Stereochemistry of the Bucherer-Bergs and Strecker Reactions of 4-*tert*-Butylcyclohexanone," *Canadian Journal of Chemistry* 53:3339-3350, National Research Council Press, CA (1975).

Harrison, H.R., et al., "Use of molecular sieves in the methyl esterification of carboxylic acids," *Chemistry and Industry* Nov. 9, 1968:1568-1568, Society of Chemical Industry, GB (1968).

Ito, M., et al. "Synthesis and Insecticidal Activity of Novel *N*-Oxydihydropyrrole Derivatives with a Substituted Spirocyclohexyl Group," *Bioscience, Biotechnology and Biochemistry* 67(6):1230-1238, Japan Society for Bioscience, Biotechnology and Agrochemistry, JP (2003).

Munday, L., "Amino-acids of the Cyclohexane Series. Part I.," *Journal of Chemical Society* 10:4372-4379, Royal Society of Chemistry, UK (1961).

Schmierer, R., and Mildenderger, H., "Cyclisierung von *N*-Acylalanin- und *N*-Acylglycinestern," *Liebigs Annalen der Chemie* 5:1095-1098, VCH Verlagsgesellschaft mbH, DE (1985).

Sonnewald, U., et al., "Transgenic tobacco plants expressing yeast-derived invertase in either the cytosol, vacuole or apoplast: a powerful tool for studying sucrose metabolism and sink/source interactions," *The Plant Journal* 1(1):95-106, Wiley-Blackwell in association with the Society for Experimental Biology, UK (1991).

Sonntag, N.O.V., "The Reactions of Aliphatic Acid Chlorides," *Chem. Reviews* 52:237-416, American Chemical Society, US (1953).

Suzuki, S., et al., "Studies on Antiviral Agents. IV. Biological Activity of Tenuazonic Acid Derivatives.," *Chemical and Pharmaceutical Bulletin* 15(8):1120-1122, The Pharmaceutical Society of Japan, Tokyo (1967).

Wolter, F.P., et al., "rbcS genes in *Solanum tuberosum*: Conservation of transit peptide and exon shuffling during evolution," *Proceedings of the National Academy of Sciences, USA* 85:846-850, National Academy of Sciences, US (1988).

International Search Report for Application No. PCT/EP2009/008260, European Patent Office, Rijswijk, Netherlands, mailed on Feb. 19, 2010.

English language translation of abstract of European Patent Publication No. EP 0 346 620 A1 (Document FP20).

Dialog File 351, Accession No. 17343120, Derwent WPI English language translation of abstract of Gennan Patent Publication No. DE 10 2005 059 892 A1 (Document FP114).

English language translation of abstract of Japanese Patent Publication No. JP 2000-053670 (Document FP79).

English language translation of abstract of Japanese Patent Publication No. JP 2002-205984 A (Document FP85).

Dialog File 351, Accession No. 3388475, Derwent WPI English language translation of abstract of Japanese Patent Publication No. JP 60-87254 A (Document FP6).

English language abstract of WO 03/059065 A1, esp@cenet Database Worldwide (2003).

Office Action mailed Dec. 3, 2008, in U.S. Appl. No. 11/666,988 (now US Patent No. 7,718,186 B2), Fischer et al., filed Nov. 28, 2007.

Office Action mailed Mar. 31, 2009, in U.S. Appl. No. 11/666,988 (now US Patent No. 7,718,186 B2), Fischer et al., filed Nov. 28, 2007.

GERMINAL ALKOXY/ALKYLSPIROCYCLIC SUBSTITUTED TETRAMATE DERIVATIVES

The present invention relates to novel geminally alkoxy/alkylspirocyclically substituted tetramic acid derivatives, to a plurality of processes for their preparation and to their use as pesticides and/or herbicides. The invention also provides selective herbicidal compositions comprising, firstly, geminally alkoxy/alkylspirocyclically substituted tetramic acid derivatives and, secondly, a crop plant compatibility-improving compound.

The present invention furthermore relates to the boosting of the action of crop protection compositions comprising, in particular, geminally alkoxy/alkylspirocyclically substituted tetramic acid derivatives, through the addition of ammonium salts or phosphonium salts and optionally penetrants, to the corresponding compositions, to processes for producing them and to their application in crop protection as insecticides and/or acaricides and/or for preventing unwanted plant growth.

Pharmaceutical properties of 3-acyl-pyrrolidine-2,4-diones have already been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-aryl-pyrrolidine-2,4-diones) of which, however, no herbicidal, insecticidal or acaricidal activity has become known. Unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (EP-A-377 893 and EP-A-442 077) are known to have herbicidal, insecticidal or acarical activity.

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869 and WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048545, DEA 102 00505 9892, WO 07/073856, WO 07/096058, WO 07/121868, WO 07/140881, WO 08/067873, WO 08/067910, WO 08/067911, WO 08/138551, WO 09/015801, WO 09/039975, WO 09/049581). Furthermore known are ketal-substituted 1H-arylpyrrolidine-2,4-diones from WO 99/16748 and (spiro)-ketal-substituted N-alkoxyalkoxy-substituted arylpyrrolidinediones from JP-A-14 205 984 and Ito M. et. al., Bioscience, Biotechnology and Biochemistry 67, 1230-1238, (2003). The addition of safeners to ketoenols is also known in principle from WO 03/013249. Moreover, WO 06/024411 discloses herbicidal compositions comprising ketoenols.

However, the herbicidal and/or acaricidal and/or insecticidal activity and/or activity spectrum and/or the plant compatibility of the known compounds, in particular with respect to crop plants, is/are not always satisfactory.

This invention, accordingly, provides novel compounds of the formula (I)

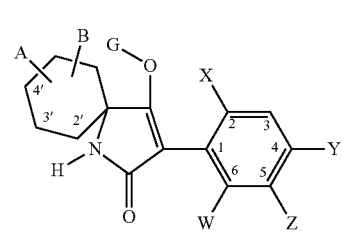

in which
W represents hydrogen, halogen, alkyl, alkenyl, alkynyl, optionally substituted cycloalkyl, alkoxy, alkenyloxy, haloalkyl, haloalkoxy or cyano,
X represents halogen, alkyl, alkenyl, alkynyl, optionally substituted cycloalkyl, alkoxy, alkenyloxy, alkylthio, alkylsulphinyl, alkylsulphonyl, haloalkyl, haloalkoxy, haloalkenyloxy, nitro or cyano,
Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl,
A represents alkoxy,
B represents alkyl, where
A and B are attached to the same carbon atom,
G represents hydrogen (a) or one of the groups

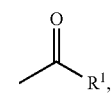

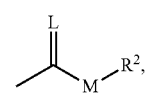

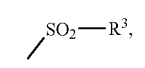

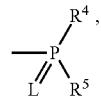

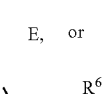

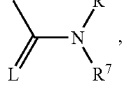

in which
E represents a metal ion or an ammonium ion,
L represents oxygen or sulphur,
M represents oxygen or sulphur,
$R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, R² represents in each case optionally halogen- or cyano-substituted alkyl, alkenyl, alkoxyalkyl or polyalkoxyalkyl or represents in each case optionally substituted cycloalkyl, phenyl or benzyl, R³, R⁴ and R⁵ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, R⁶ and R⁷ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulphur.

Depending, inter alia, on the nature of the substituents, the compounds of the formula (I) can be present as optical isomers or mixtures of isomers in varying compositions, which can be separated, if desired, in a customary manner. The present invention provides both the pure isomers and the isomer mixtures, their preparation and use and compositions comprising them. However, the following text will, for the sake of simplicity, always mention compounds of the formula (I), even though this is understood as meaning not only the pure compounds, but also, if appropriate, mixtures with various amounts of isomeric compounds.

Taking into consideration the various meanings (a), (b), (c), (d), (e), (f) and (g) of group G, the following main structures (I-a) to (I-g) result

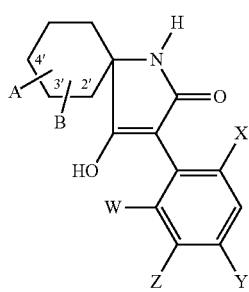

(I-a)

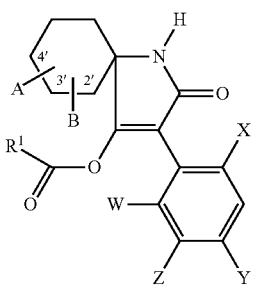

(I-b)

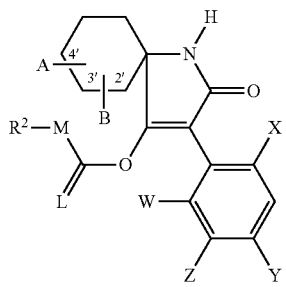

(I-c)

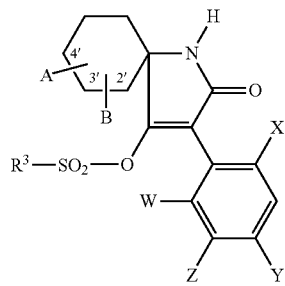

(I-d)

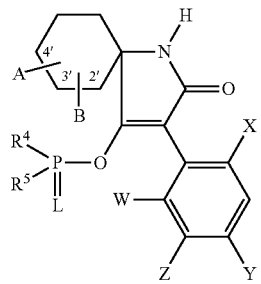

(I-e)

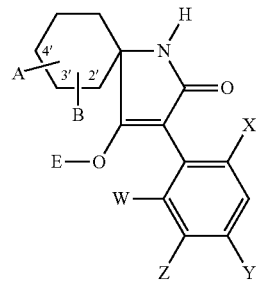

(I-f)

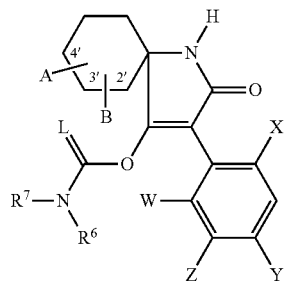

(I-g)

in which

A, B, E, L, M, W, X, Y, Z, R¹, R², R³, R⁴, R⁵, R⁶ and R⁷ have the abovementioned meanings.

Furthermore, it has been found that the novel compounds of the formula (I) are obtained by the processes described below:

(A) Compounds of the formula (I-a)

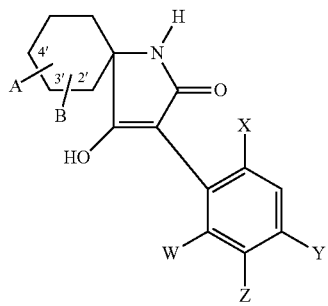

(I-a)

in which
A, B, W, X, Y and Z have the meanings given above,
are obtained when
compounds of the formula (II)

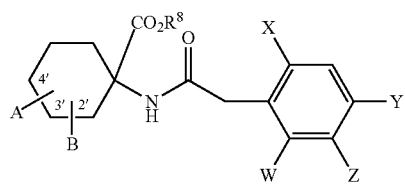

(II)

in which
A, B, W, X, Y and Z have the meanings given above,
and
$R^8$ represents alkyl (preferably $C_1$-$C_6$-alkyl)
are subjected to an intramolecular condensation reaction in the presence of a diluent and in the presence of a base.

Moreover, it has been found
(B) that the compounds of the formula (I-b) shown above in which $R^1$, A, B, W, X, Y and Z have the meanings given above are obtained when compounds of the formula (I-a) shown above in which A, B, W, X, Y and Z have the meanings given above are in each case
α) reacted with compounds of the formula (III)

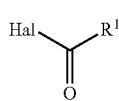

(III)

in which
$R^4$ has the meaning given above and
Hal represents halogen (in particular chlorine or bromine)
or
β) with carboxylic anhydrides of the formula (IV)

$R^1$—CO—O—CO—$R^1$ (IV)

in which
$R^1$ has the meaning given above,
if appropriate in the presence of a diluent and if appropriate in the presence of an acid binder;
(C) that the compounds of the formula (I-c) shown above in which $R^2$, A, B, M, W, X, Y and Z have the meanings given above and L represents oxygen are obtained when compounds of the formula (I-a) shown above in which A, B, W, X, Y and Z have the meanings given above are in each case reacted with chloroformic esters or chloroformic thioesters of the formula (V)

$R^2$-M-CO—Cl (V)

in which
$R^2$ and M have the meanings given above,
if appropriate in the presence of a diluent and if appropriate in the presence of an acid binder;
(D) that compounds of the formula (I-c) shown above in which $R^2$, A, B, M, W, X, Y and Z have the meanings given above and L represents sulphur are obtained when compounds of the formula (I-a) shown above in which A, B, W, X, Y and Z have the meanings given above are in each case reacted with chloromonothioformic esters or chlorodithioformic esters of the formula (VI)

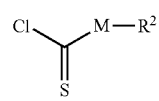

(VI)

in which
M and $R^2$ have the meanings given above,
if appropriate in the presence of a diluent and if appropriate in the presence of an acid binder,
(E) that compounds of the formula (I-d) shown above in which $R^3$, A, B, W, X, Y and Z have the meanings given above are obtained when compounds of the formula (I-a) shown above in which A, B, W, X, Y and Z have the meanings given above are in each case
reacted with sulphonyl chlorides of the formula (VII)

$R^3$—$SO_2$—Cl (VII)

in which
$R^3$ has the meaning given above,
if appropriate in the presence of a diluent and if appropriate in the presence of an acid binder,
(F) that compounds of the formula (I-e) shown above in which L, $R^4$, $R^5$, A, B, W, X, Y and Z have the meanings given above are obtained when compounds of the formula (I-a) shown above in which A, B, W, X, Y and Z have the meanings given above are in each case
reacted with phosphorus compounds of the formula (VIII)

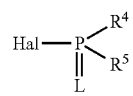

(VIII)

in which
L, $R^4$ and $R^5$ have the meanings given above and
Hal represents halogen (in particular chlorine or bromine),
if appropriate in the presence of a diluent and if appropriate in the presence of an acid binder,
(G) that compounds of the formula (I-f) shown above in which E, A, B, W, X, Y and Z have the meanings given above are obtained when compounds of the formula (I-a) in which A, B, W, X, Y and Z have the meanings given above are in each case
reacted with metal compounds or amines of the formula (IX) or (X)

$Me(OR^{10})_t$ (IX)

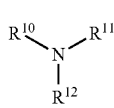
(X)

in which
Me represents a monovalent or divalent metal (preferably an alkali metal or alkaline earth metal such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl)
if appropriate in the presence of a diluent,
(H) that compounds of the formula (I-g) shown above in which L, $R^6$, $R^7$, A, B, W, X, Y and Z have the meanings given above are obtained when compounds of the formula (I-a) shown above in which A, B, W, X, Y and Z have the meanings given above are in each case
α) reacted with isocyanates or isothiocyanates of the formula (XI)

$$R^6—N=C=L \quad (XI)$$

in which
$R^6$ and L have the meanings given above,
if appropriate in the presence of a diluent and if appropriate in the presence of a catalyst, or
β) reacted with carbamoyl chlorides or thiocarbamoyl chlorides of the formula (XII)

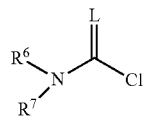
(XII)

in which
L, $R^6$ and $R^7$ have the meanings given above,
if appropriate in the presence of a diluent and if appropriate in the presence of an acid binder,
(Iα) that compounds of the formulae (I-a) to (I-g) shown above in which A, B, G, W, X, Y and Z have the meaning given above are obtained when compounds of the formulae (I-a') to (I-g') in which A, B, G, W, X and Y have the meaning given above and Z' preferably represents bromine or iodine

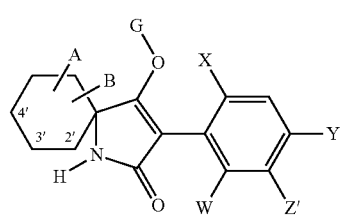
(I-a' to I-g')

and
(Iβ) that compounds of the formulae (I-a) to (I-g) shown above in which A, B, G, W, X, Y and Z have the meaning given above are obtained when compounds of the formulae (I-a") to (I-g") in which A, B, G, W, X and Y have the meaning given above and Y' preferably represents bromine or iodine

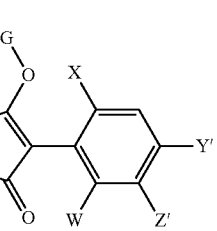
(I-a" to I-g")

are coupled with (het)aryl derivatives capable of coupling, for example phenylboronic acids of the formulae (XIIIα) and (XIIIβ)

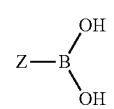
(XIIIα)

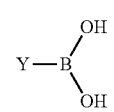
(XIIIβ)

or esters thereof, in the presence of a solvent, in the presence of a catalyst (for example Pd complexes) and in the presence of a base (for example sodium carbonate, potassium phosphate).

Furthermore, it has been found that the new compounds of the formula (I) have very good activity as pesticides, preferably as insecticides, acaricides and also herbicides.

Surprisingly, it has now also been found that certain substituted cyclic ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soya beans and rice.

The invention also provides selective herbicidal compositions comprising an effective amount of an active compound combination comprising, as components,
a') at least one compound of the formula (I) in which A, B, G, W, X, Y and Z have the meaning given above and
(b') at least one crop plant compatibility-improving compound (safener).

The safeners are preferably selected from the group consisting of:
S1) compounds of the formula (S1)

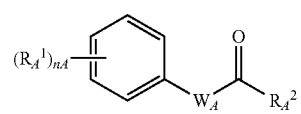
(S1)

where the symbols and indices have the following meanings:
$n_A$ represents a natural number from 0 to 5, preferably from 0 to 3;
$R_A^1$ represents halogen, $(C_1$-$C_4)$-alkyl, $(C_1$-$C_4)$-alkoxy, nitro or $(C_1$-$C_4)$-haloalkyl;

$W_A$ represents an unsubstituted or substituted divalent heterocyclic radical from the group consisting of partially unsaturated or aromatic five-membered heterocycles having 1 to 3 hetero ring atoms from the group consisting of N and O, where at least one nitrogen atom and at most one oxygen atom is present in the ring, preferably a radical from the group consisting of ($W_A^1$) to ($W_A^4$),

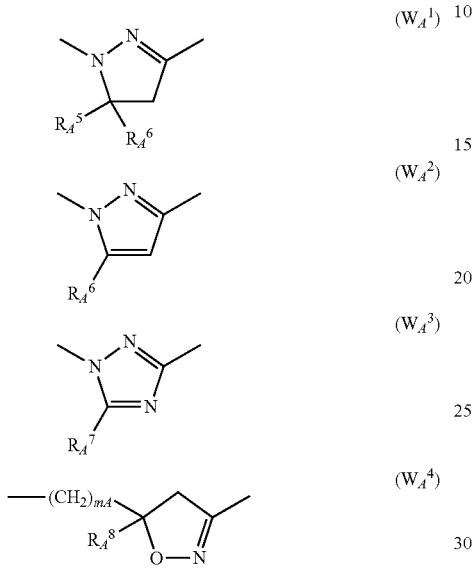

$m_A$ represents 0 or 1;
$R_A^2$ represents $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S-1) and which is unsubstituted or substituted by radicals from the group consisting of $(C_1$-$C_4)$-alkyl, $(C_1$-$C_4)$-alkoxy and optionally substituted phenyl, preferably a radical of the formula $OR_A^3$, $NHR_A^4$ or $N(CH_3)_2$, in particular of the formula $OR_A^3$;
$R_A^3$ represents hydrogen or an unsubstituted or substituted aliphatic hydrocarbon radical having preferably a total of 1 to 18 carbon atoms;
$R_A^4$ represents hydrogen, $(C_1$-$C_6)$-alkyl, $(C_1$-$C_6)$-alkoxy or substituted or unsubstituted phenyl;
$R_A^5$ represents H, $(C_1$-$C_8)$-alkyl, $(C_1$-$C_8)$-haloalkyl, $(C_1$-$C_4)$-alkoxy-$(C_1$-$C_8)$-alkyl, cyano or $COOR_A^9$ where $R_A^9$ represents hydrogen, $(C_1$-$C_8)$-alkyl, $(C_1$-$C_8)$-haloalkyl, $(C_1$-$C_4)$-alkoxy-$(C_1$-$C_4)$-alkyl, $(C_1$-$C_6)$-hydroxyalkyl, $(C_3$-$C_{12})$-cycloalkyl or tri-$(C_1$-$C_4)$-alkylsilyl;
$R_A^6$, $R_A^7$, $R_A^8$ are identical or different and represent hydrogen, $(C_1$-$C_8)$-alkyl, $(C_1$-$C_8)$-haloalkyl, $(C_3$-$C_{12})$-cycloalkyl or substituted or unsubstituted phenyl;
preferably:
a) compounds of the type of the dichlorophenylpyrazoline-3-carboxylic acid ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;
b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;
c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;
d) compounds of the type of the triazolecarboxylic acids ($S1^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;
e) compounds of the type of the 5-benzyl- or 5-phenyl-2-isoxazoline-3-carboxylic acid or the 5,5-diphenyl-2-isoxazoline-3-carboxylic acid ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in the patent application WO-A-95/07897.
S2) Quinoline derivatives of the formula (S2),

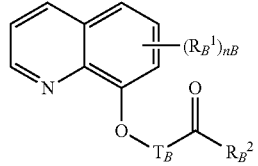

where the symbols and indices have the following meanings:
$R_B^1$ represents halogen, $(C_1$-$C_4)$-alkyl, $(C_1$-$C_4)$-alkoxy, nitro or $(C_1$-$C_4)$-haloalkyl;
$n_B$ represents a natural number from 0 to 5, preferably from 0 to 3;
$R_B^2$ represents $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of $(C_1$-$C_4)$-alkyl, $(C_1$-$C_4)$-alkoxy and optionally substituted phenyl, preferably a radical of the formula $OR_B^3$, $NHR_B^4$ or $N(CH_3)_2$, in particular of the formula $OR_B^3$;
$R_B^3$ represents hydrogen or an unsubstituted or substituted aliphatic hydrocarbon radical having preferably a total of 1 to 18 carbon atoms;
$R_B^4$ represents hydrogen, $(C_1$-$C_6)$-alkyl, $(C_1$-$C_6)$-alkoxy or substituted or unsubstituted phenyl;
$T_B$ represents a $(C_1$- or $C_2)$-alkanediyl chain which is unsubstituted or substituted by one or two $(C_1$-$C_4)$-alkyl radicals or by [$(C_1$-$C_3)$-alkoxy]carbonyl;

preferably:
a) compounds of the type of the 8-quinolinoxyacetic acid (S2a), preferably
1-methylhexyl (5-chloro-8-quinolinoxy)acetate (common name "cloquintocet-mexyl") (S2-1),
1,3-dimethylbut-1-yl (5-chloro-8-quinolinoxy)acetate (S2-2),
4-allyloxybutyl (5-chloro-8-quinolinoxy)acetate (S2-3),
1-allyloxyprop-2-yl (5-chloro-8-quinolinoxy)acetate (S2-4),
ethyl (5-chloro-8-quinolinoxy)acetate (S2-5),
methyl (5-chloro-8-quinolinoxy)acetate (S2-6),
allyl (5-chloro-8-quinolinoxy)acetate (S2-7),
2-(2-propylideneiminoxy)-1-ethyl (5-chloro-8-quinolinoxy) acetate (S2-8), 2-oxo-prop-1-yl(5-chloro-8-quinolinoxy) acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminium, iron, ammonium, quaternary ammonium, sulphonium or phosphonium salts, as described in WO-A-2002/34048;
b) compounds of the type of the (5-chloro-8-quinolinoxy) malonic acid (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

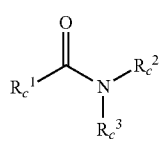

(S3)

where the symbols and indices have the following meanings:
$R_C^1$ represents $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and represent hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;
preferably:
active compounds of the type of the dichloroacetamides which are frequently used as pre-emergence safeners (soil-acting safeners), such as, for example,
"dichlormid" (N,N-diallyl-2,2-dichloroacetamide) (S3-1),
"R-29148" (3-dichloroacetyl-2,2,5-trimethyl-1,3-oxazolidine) from Stauffer (S3-2),
"R-28725" (3-dichloroacetyl-2,2-dimethyl-1,3-oxazolidine) from Stauffer (S3-3),
"benoxacor" (4-dichloroacetyl-3,4-dihydro-3-methyl-2H-1,4-benzoxazine) (S3-4),
"PPG-1292" (N-allyl-N-[(1,3-dioxolan-2-yl)methyl]dichloroacetamide) from PPG Industries (S3-5),
"DKA-24" (N-allyl-N-[(allylaminocarbonyl)methyl]dichloroacetamide) from Sagro-Chem (S3-6),
"AD-67" or "MON 4660" (3-dichloroacetyl-1-oxa-3-azaspiro[4,5]decane) from Nitrokemia or Monsanto (S3-7),
"TI-35" (1-dichloroacetylazepane) from TRI-Chemical RT (S3-8), "diclonon" (dicyclonone) or "BAS145138" or "LAB145138" (S3-9)
(3-dichloroacetyl-2,5,5-trimethyl-1,3-diazabicyclo[4.3.0] nonane) from BASF, "furilazole" or "MON 13900" ((RS)-3-dichloroacetyl-5-(2-furyl)-2,2-dimethyloxazolidine) (S3-10) and also its (R)-isomer (S3-11).

S4) N-Acylsulphonamides of the formula (S4) and their salts,

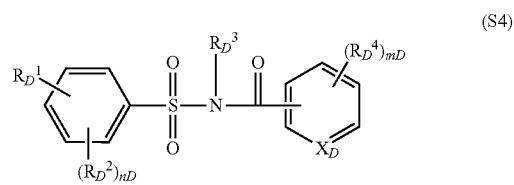

(S4)

where the symbols and indices have the following meanings:
$X_D$ represents CH or N;
$R_D^1$ represents CO—$NR_D^5R_D^6$ or NHCO—$R_D^7$;
$R_D^2$ represents halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;
$R_D^3$ represents hydrogen, $(C_1-C_4)$-alkyl, $(C_2-C_4)$-alkenyl or $(C_2-C_4)$-alkynyl;
$R_D^4$ represents halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;
$R_D^5$ represents hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ represents hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or
$R_D^5$ and $R_D^6$ together with the nitrogen atom carrying them form a pyrrolidinyl or piperidinyl radical;
$R_D^7$ represents hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $V_D$ substituents from the group consisting of halogen, $(C_1-C_4$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;
$n_D$ represents 0, 1 or 2;
$m_D$ represents 1 or 2;

$v_D$ represents 0, 1, 2 or 3;

from among these, preference is given to compounds of the type of the N-acylsulphonamides, for example of the formula (S4$^a$) below, which are known, for example, from WO-A-97/45016

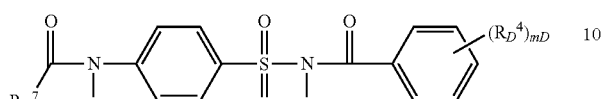

(S4a)

in which $R_D^7$ represents $(C_1-C_6)$-alkyl, $(C_3-C_6)$-cycloalkyl, where the 2 last-mentioned radicals are substituted by $v_D$ substituents from the group consisting of halo, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;

$R_D^4$ represents halogen, $(C_1-C_4)$-alkyl, $(C_1-C_4)$-alkoxy, $CF_3$;

$m_D$ 1 or 2;

$v_D$ represents 0, 1, 2 or 3;

and also acylsulphamoylbenzamides, for example of the formula (S4$^b$) below, which are known, for example, from WO-A-99/16744,

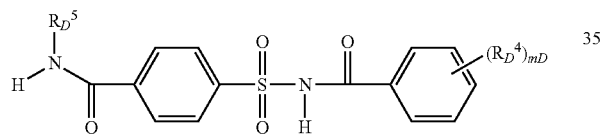

(S4b)

for example those in which $R_D^5$=cyclopropyl and $(R_D^4)$=2-OMe ("cyprosulphamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-Cl-2-OMe (S4-4) and $R_D^5$=isopropyl and $(R_D^4)$=2-OMe (S4-5)

and also compounds of the type of the N-acylsulphamoylphenylureas of the formula (S4$^c$), which are known, for example, from EP-A-365484,

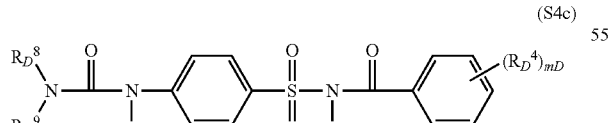

(S4c)

in which $R_D^8$ and $R_D^9$ independently of one another represent hydrogen, $(C_1-C_8)$-alkyl, $(C_3-C_8)$-cycloalkyl, $(C_3-C_6)$-alkenyl, $(C_3-C_6)$-alkynyl, $R_D^4$ represents halogen, $(C_1-C_4)$-alkyl, $(C_1-C_4)$-alkoxy, $CF_3$, $m_D$ represents 1 or 2;

for example

1-[4-(N-2-methoxybenzoylsulphamoyl)phenyl]-3-methylurea,

1-[4-(N-2-methoxybenzoylsulphamoyl)phenyl]-3,3-dimethylurea,

1-[4-(N-4,5-dimethylbenzoylsulphamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2 (1H)-one, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

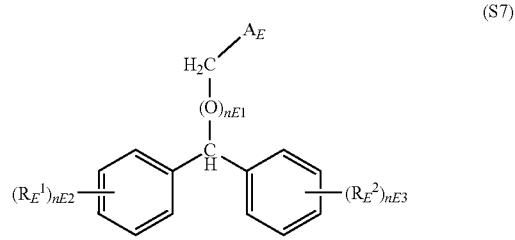

(S7)

where the symbols and indices have the following meanings:

$R_E^1$, $R_E^2$ independently of one another represent halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ represents $COOR_E^3$ or $COSR_E^4$ $R_E^3$, $R_E^4$ independently of one another represent hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ represents 0 or 1;

$n_E^2$, $n_E^3$ independently of one another represent 0, 1 or 2, preferably:

diphenylmethoxyacetic acid, ethyl diphenylmethoxyacetate, methyl diphenylmethoxyacetate (CAS Reg. No. 41858-19-9) (S7-1).

S8) Compounds of the formula (S8), as described in WO-A-98/27049

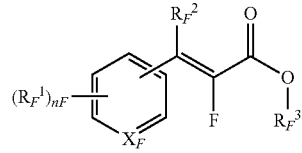
(S8)

in which $X_F$ represents CH or N, $n_F$ represents, if $X_F$=N, an integer from 0 to 4 and represents, if $X_F$=CH, an integer from 0 to 5, $R_F^1$ represents halogen, $(C_1$-$C_4)$-alkyl, $(C_1$-$C_4)$-haloalkyl, $(C_1$-$C_4)$-alkoxy, $(C_1$-$C_4)$-haloalkoxy, nitro, $(C_1$-$C_4)$-alkylthio, $(C_1$-$C_4)$-alkylsulphonyl, $(C_1$-$C_4)$-alkoxycarbonyl, optionally substituted phenyl, optionally substituted phenoxy, $R_F^2$ represents hydrogen or $(C_1$-$C_4)$-alkyl, $R_F^3$ represents hydrogen, $(C_1$-$C_8)$-alkyl, $(C_2$-$C_4)$-alkenyl, $(C_2$-$C_4)$-alkynyl or aryl, where each of the carbon-containing radicals mentioned above is unsubstituted or substituted by one or more, preferably by up to three, identical or different radicals from the group consisting of halogen and alkoxy; or salts thereof, preferably compounds in which $X_F$ represents CH, $n_F$ represents an integer from 0 to 2, $R_F^1$ represents halogen, $(C_1$-$C_4)$-alkyl, $(C_1$-$C_4)$-haloalkyl, $(C_1$-$C_4)$-alkoxy, $(C_1$-$C_4)$-haloalkoxy, $R_F^2$ is hydrogen or $(C_1$-$C_4)$-alkyl, $R_F^3$ represents hydrogen, $(C_1$-$C_8)$-alkyl, $(C_2$-$C_4)$-alkenyl, $(C_2$-$C_4)$-alkynyl or aryl, where each of the carbon-containing radicals mentioned above is unsubstituted or substituted by one or more, preferably by up to three, identical or different radicals from the group consisting of halogen and alkoxy; or salts thereof, S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999/000020.

S10) Compounds of the formula (S10$^a$) or (S10$^b$)
as described in WO-A-2007/023719 and WO-A-2007/023764

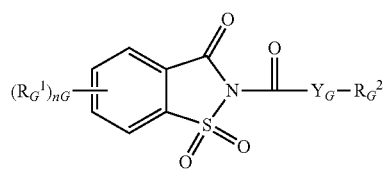
(S10a)

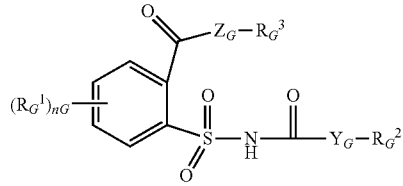
(S10b)

in which $R_G^1$ represents halogen, $(C_1$-$C_4)$-alkyl, methoxy, nitro, cyano, $CF_3$, $OCF_3$ $Y_G$, $Z_G$ independently of one another are O or S, $n_G$ represents an integer from 0 to 4, $R_G^2$ is $(C_1$-$C_{16})$-alkyl, $(C_2$-$C_6)$-alkenyl, $(C_3$-$C_6)$-cycloalkyl, aryl; benzyl, halobenzyl, $R_G^3$ represents hydrogen or $(C_1$-$C_6)$-alkyl.

S11) Active compounds of the type of the oxyimino compounds (S11), which are known as seed dressings, such as, for example, "oxabetrinil" ((Z)-1,3-dioxolan-2-ylmethoxyimino (phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and "cyometrinil" or "CGA-43089" ((Z)-cyanomethoxyimino(phenyl)acetonitrile) (S11-3), which is known as seed dressing safener for millet against metolachlor damage.

S12) Active compounds from the class of the isothiochromanones (S12), such as, for example, methyl [(3-oxo-1H-2-benzothiopyran-4(3H)-ylidene)methoxy]acetate (CAS Reg. No.: 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as seed dressing safener for maize against thiocarbamate herbicide damage, "fenclorim" (4,6-dichloro-2-phenylpyrimidine) (S13-2), which is known as safener for retilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL304415" (CAS Reg. No.: 31541-57-8) (4-carboxy-3,4-dihydro-2H-1-benzopyran-4-acetic acid) (S13-4) from American Cyanamid, which is known as safener for maize against imidazolinone damage, "MG191" (CAS Reg. No.: 96420-72-3) (2-dichloromethyl-2-methyl-1,3-dioxolane) (S13-5) from Nitrokemia, which is known as safener for maize, "MG-838" (CAS Reg. No.: 133993-74-5) (2-propenyl 1-oxa-4-azaspiro[4.5]decane-4-carbodithioate) (S13-6) from Nitrokemia, "disulphoton" (O,O-diethyl S-2-ethylthioethyl phosphorodithioate) (S13-7), "dietholate" (O,O-diethyl 0-phenyl phosphorothioate) (S13-8), "mephenate" (4-chlorophenyl methylcarbamate) (S13-9).

S14) Active compounds which, besides a herbicidal effect against harmful plants, also have a safener effect on crop plants such as rice, such as, for example, "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulphuron herbicide damage, "cumyluron"="JC-940" (3-(2-chlorophenylmethyl)-1-(1-methyl-1-phenyl-ethyl)urea, see JP-A-60087254), which is known as safener for rice against damage by some herbicides, "methoxyphenone" or "NK 049" (3,3'-dimethyl-4-methoxybenzophenone), which is known as safener for rice against damage by some herbicides, "CSB" (1-bromo-4-(chloromethylsulphonyl)benzene) from Kumiai, (CAS Reg. No.: 54091-06-4), which is known as safener for rice against damage by some herbicides.

S15) Active compounds which are primarily used as herbicides, but also have safener effect on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Most preferred as crop plant compatibility-improving compound [component (b')] are cloquintocet-mexyl, fenchlorazole-ethyl, isoxadifen-ethyl, mefenpyr-diethyl, fenclorim, cumyluron, S4-1 and S4-5, and particular emphasis is given to cloquintocet-mexyl and mefenpyr-diethyl.

Surprisingly, it has now been found that the active compound combinations defined above of compounds of the general formula (I) and safeners (antidotes) from the group (b') set out above combine very good useful plant tolerance with a particularly high herbicidal activity and can be used in various crops, in particular in cereals (especially wheat), but also in soya, potatoes, maize and rice, for the selective control of weeds.

In this context it is to be considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of compounds of the formula (I) on the crop plants, without at the same time having any critical adverse effect on the herbicidal activity against the weeds.

Emphasis may be given here to the particularly advantageous effect of the particularly preferred and most preferred combination partners from group (b'), in particular with regard to the gentle treatment of cereal plants, such as wheat, barley and rye, for example, but also maize and rice, as crop plants.

The formula (I) provides a general definition of the compounds according to the invention. Preferred substituents or ranges of the radicals given under the formulae shown above and below are illustrated below:

W preferably represents hydrogen, halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents $C_1$-$C_6$-alkoxy, $C_1$-$C_4$-haloalkyl, $C_1$-$C_4$-haloalkoxy or cyano, X preferably represents halogen, $C_1$-$C_6$-alkyl, $C_2$-$C_6$-alkenyl, $C_2$-$C_6$-alkynyl, represents $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represents $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro or cyano, Y and Z independently of one another preferably represent hydrogen, halogen, $C_1$-$C_6$-alkyl, $C_2$-$C_6$-alkenyl, $C_2$-$C_6$-alkynyl, represent $C_3$-$C_6$-cycloalkyl which is optionally mono- or disubstituted by $C_1$-$C_2$-alkyl, $C_1$-$C_2$-alkoxy, fluorine, chlorine, trifluoromethyl or $C_3$-$C_6$-cycloalkyl, represent $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or represent one of the (het)aryl radicals

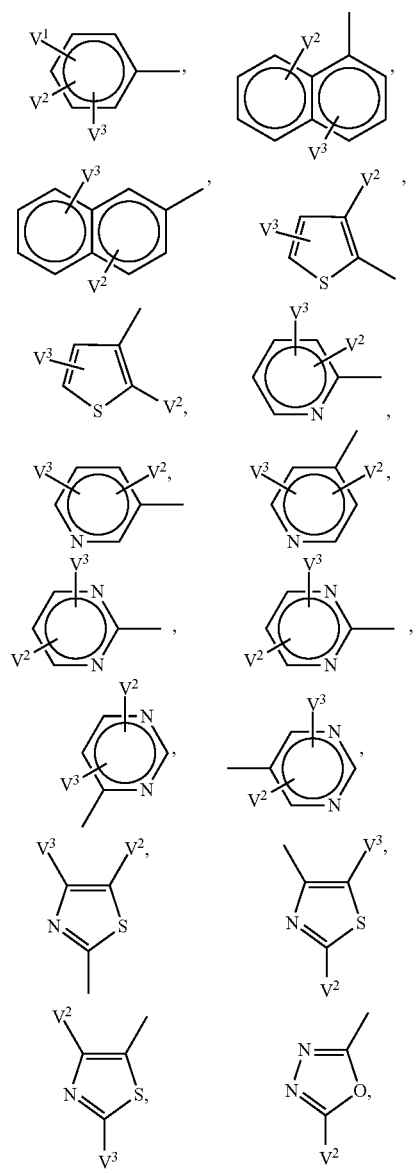

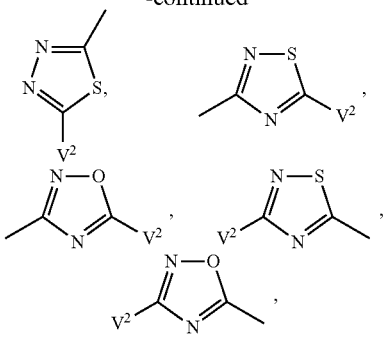

where in the case of (het)aryl only one of the radicals Y or Z may represent (het)aryl, $V^1$ preferably represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-halogenoalkyl, $C_1$-$C_4$-halogenoalkoxy, nitro, cyano, or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally monosubstituted or polysubstituted by halogen, $C_1$-$C_6$-alkyl, $C_1$-$C_6$-alkoxy, $C_1$-$C_4$-halogenoalkyl, $C_1$-$C_4$-halogenoalkoxy, nitro or cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, A preferably represents $C_1$-$C_6$-alkoxy, B preferably represents $C_1$-$C_6$-alkyl, where A and B are attached to the same carbon atom, G preferably represents hydrogen (a) or represents one of the groups

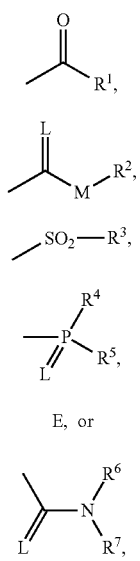

in which

E represents a metal ion or an ammonium ion,

L represents oxygen or sulphur and

M represents oxygen or sulphur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents phenyl which is optionally substituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio or $C_1$-$C_6$-alkylsulphonyl, represents phenyl-$C_1$-$C_6$-alkyl which is optionally substituted by halogen, nitro, cyano, $C_1$-$C_6$-alkyl, $C_1$-$C_6$-alkoxy, $C_1$-$C_6$-halogenoalkyl or $C_1$-$C_6$-halogenoalkoxy, represents optionally halogen- or $C_1$-$C_6$-alkyl-substituted 5- or 6-membered hetaryl having one or two heteroatoms from the group consisting of oxygen, sulphur and nitrogen, represents phenoxy-$C_1$-$C_6$-alkyl which is optionally substituted by halogen or $C_1$-$C_6$-alkyl, represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen.

$R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, or represents $C_3$-$C_8$-cycloalkyl which is optionally substituted by halogen, $C_1$-$C_6$-alkyl or $C_1$-$C_6$-alkoxy, or represents phenyl or benzyl, each of which is optionally substituted by halogen, cyano, nitro, $C_1$-$C_6$-alkyl, $C_1$-$C_6$-alkoxy, $C_1$-$C_6$-halogenoalkyl or $C_1$-$C_6$-halogenalkoxy, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-halogenoalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_2$-haloalkyl or $C_1$-$C_2$-haloalkoxy, X particularly preferably represents chlorine, bromine, iodine, $C_1$-$C_4$-alkyl, $C_2$-$C_4$-alkenyl, $C_2$-$C_4$-alkynyl, represents $C_3$-$C_6$-cycloalkyl which is optionally monosubstituted by methyl, ethyl, methoxy, fluorine, chlorine, trifluoromethyl or cyclopropyl, represents $C_1$-$C_4$-alkoxy, $C_1$-$C_4$-haloalkyl, $C_1$-$C_4$-haloalkoxy or cyano, Y and Z independently of one another particularly preferably represent hydrogen, fluorine, chlorine, bromine, iodine, $C_1$-$C_1$-alkyl, $C_2$-$C_4$-alkenyl, $C_2$-$C_4$-alkynyl, represent $C_3$-$C_6$-cycloalkyl which is optionally monosubstituted by methyl, ethyl, methoxy, fluorine, chlorine, trifluoromethyl or cyclopropyl, represents $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or represent one of the (het)aryl radicals,

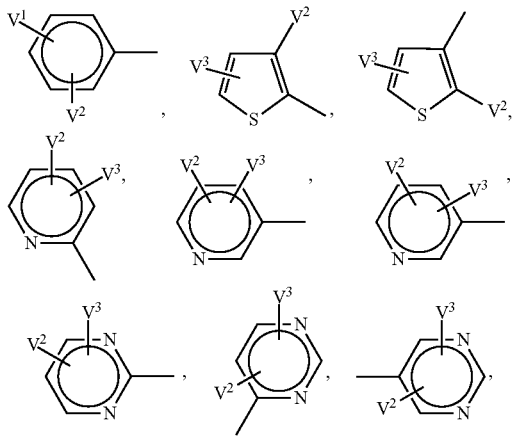

where in the case of (het)aryl only one of the radicals Y or Z may represent (het)aryl, $V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or represents phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A particularly preferably represents $C_1$-$C_4$-alkoxy, B particularly preferably represents $C_1$-$C_4$-alkyl, where A and B are attached to the same carbon atom, G particularly preferably represents hydrogen (a) or represents one of the groups

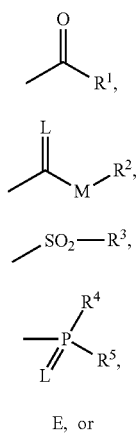

E, or

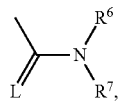

in which

E represents a metal ion or an ammonium ion,

L represents oxygen or sulphur and

M represents oxygen or sulphur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent hydrogen, represent $C_1$-$C_6$-alkyl, $C_3$-$C_6$- cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, vinyl, ethynyl, propynyl, cyclopropyl, methoxy, ethoxy or trifluoromethyl, X very particularly preferably represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another very particularly preferably represent hydrogen, fluorine, chlorine, bromine, iodine, methyl, ethyl, vinyl, ethynyl, propynyl, cyclopropyl, methoxy, trifluoromethyl, trifluoromethoxy, cyano or a phenyl radical,

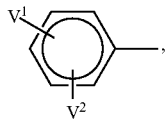

where in the case of phenyl only one of the radicals Y or Z may represent phenyl, $V^1$ very particularly preferably represents hydrogen, fluorine or chlorine, $V^2$ very particularly preferably represents hydrogen, fluorine, chlorine, methyl, ethyl, n-propyl, isopropyl, methoxy, ethoxy or trifluoromethyl, A very particularly preferably represents methoxy, ethoxy or propoxy, B very particularly preferably represents methyl, ethyl or propyl, where A and B are attached to the same carbon atom, with the 3'-position or the 4'-position being preferred, G very particularly preferably represents hydrogen (a) or represents one of the groups

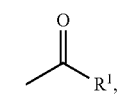 (b)

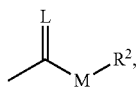 (c)

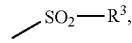 (d)

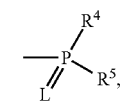 (e)

(f)

E, or

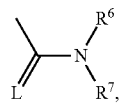 (g)

in which

E represents a metal ion or an ammonium ion,

L represents oxygen or sulphur and

M represents oxygen or sulphur, $R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy, represents furanyl, thienyl or pyridyl, each of which is optionally monosubstituted by chlorine, bromine or methyl, $R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl or represents phenyl or benzyl, each of which is optionally mono- or disubstituted by fluorine, chlorine, cyano, nitro, methyl, ethyl, methoxy, trifluoromethyl or trifluoromethoxy, $R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another very particularly preferably represent hydrogen, represent $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulphur.

W especially preferably represents hydrogen, chlorine, bromine, methyl, ethyl or methoxy, (with emphasis hydrogen, methyl or ethyl), X especially preferably represents chlorine, bromine, methyl, ethyl, methoxy or ethoxy, Y and Z independently of one another especially preferably represent hydrogen, chlorine, bromine, methyl or represent the radical

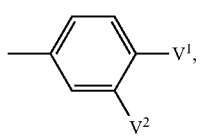

where in this case only one of the radicals Y or Z may represent

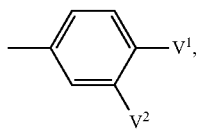

V¹ especially preferably represents fluorine or chlorine,
V² especially preferably represents hydrogen, fluorine or chlorine, (with emphasis hydrogen),
A especially preferably represents methoxy or ethoxy,
especially preferably represents methyl, ethyl or propyl, where A and B are attached to the same carbon atom in the 4'-position,
G especially preferably represents hydrogen (a) or represents one of the groups

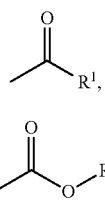

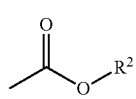

or E(f)
in which
E represents a metal ion or an ammonium ion,
R¹ especially preferably represents $C_1$-$C_{10}$-alkyl, $C_1$-$C_4$-alkoxy-$C_1$-$C_2$-alkyl, $C_3$-$C_6$-cycloalkyl,
represents phenyl which is optionally monosubstituted by chlorine, or represents thienyl, (with emphasis $C_1$-$C_{10}$-alkyl),
R² especially preferably represents $C_1$-$C_{10}$-alkyl, $C_2$-$C_{10}$-alkenyl, or represents benzyl, (with emphasis $C_1$-$C_{10}$-alkyl).

The abovementioned general or preferred radical definitions or illustrations can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Emphasis is given to compounds of the formula (I) in which G represents hydrogen.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

In addition to the compounds mentioned in the Preparation Examples, the following compounds of the formula (I-a) may be specifically mentioned:

TABLE 1

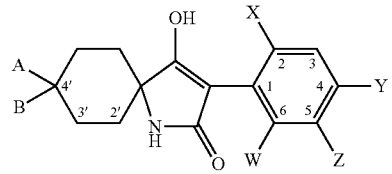

(I-a)

| A | B | X | W | Y | Z |
|---|---|---|---|---|---|
| OCH₃ | CH₃ | CH₃ | H | H | H |
| OCH₃ | CH₃ | Br | H | H | H |
| OCH₃ | CH₃ | Cl | H | H | H |
| OCH₃ | CH₃ | CF₃ | H | H | H |
| OCH₃ | CH₃ | OCH₃ | H | H | H |
| OCH₃ | CH₃ | Br | H | Cl | H |
| OCH₃ | CH₃ | Cl | H | Br | H |
| OCH₃ | CH₃ | Cl | H | Cl | H |
| OCH₃ | CH₃ | Cl | H | CH | H |
| OCH₃ | CH₃ | CH₃ | H | Cl | H |
| OCH₃ | CH₃ | Cl | Cl | H | H |
| OCH₃ | CH₃ | Cl | OCH₃ | H | H |
| OCH₃ | CH₃ | Cl | CH₃ | H | H |
| OCH₃ | CH₃ | Cl | OC₂H₅ | H | H |
| OCH₃ | CH₃ | OCH₃ | OCH₃ | H | H |
| OCH₃ | CH₃ | CH₃ | CH₃ | H | H |
| OCH₃ | CH₃ | C₂H₅ | CH₃ | H | H |
| OCH₃ | CH₃ | C₂H₅ | C₂H₅ | H | H |
| OCH₃ | CH₃ | Br | CH₃ | Br | H |
| OCH₃ | CH₃ | Cl | CH₃ | Cl | H |
| OCH₃ | CH₃ | CH₃ | Br | CH₃ | H |
| OCH₃ | CH₃ | CH₃ | Cl | CH₃ | H |
| OCH₃ | CH₃ | OCH₃ | CH₃ | CH₃ | H |
| OCH₃ | CH₃ | OC₂H₅ | CH₃ | CH₃ | H |
| OCH₃ | CH₃ | OC₃H₇ | CH₃ | CH₃ | H |
| OCH₃ | CH₃ | CH₃ | CH₃ | CH₃ | H |
| OCH₃ | CH₃ | Br | Br | CH₃ | H |
| OCH₃ | CH₃ | Cl | Cl | CH₃ | H |
| OCH₃ | CH₃ | CH₃ | CH₃ | Br | H |
| OCH₃ | CH₃ | OCH₃ | C₂H₅ | CH₃ | H |
| OCH₃ | CH₃ | OC₂H₅ | C₂H₅ | CH₃ | H |
| OCH₃ | CH₃ | CH₃ | CH₃ | OCH₃ | H |
| OCH₃ | CH₃ | Br | Cl | CH₃ | H |
| OCH₃ | CH₃ | Br | CH₃ | Cl | H |
| OCH₃ | CH₃ | Cl | CH₃ | Br | H |
| OCH₃ | CH₃ | CH₃ | CH₃ | Cl | H |
| OCH₃ | CH₃ | C₂H₅ | CH₃ | CH₃ | H |
| OCH₃ | CH₃ | C₂H₅ | C₂H₅ | CH₃ | H |
| OCH₃ | CH₃ | C₂H₅ | CH₃ | C₂H₅ | H |
| OCH₃ | CH₃ | C₂H₅ | C₂H₅ | C₂H₅ | H |
| OCH₃ | CH₃ | C₂H₅ | CH₃ | Cl | H |
| OCH₃ | CH₃ | C₂H₅ | C₂H₅ | Cl | H |
| OCH₃ | CH₃ | C₂H₅ | CH₃ | Br | H |
| OCH₃ | CH₃ | C₂H₅ | C₂H₅ | Br | H |
| OCH₃ | CH₃ | C₂H₅ | Cl | CH₃ | H |

TABLE 1-continued

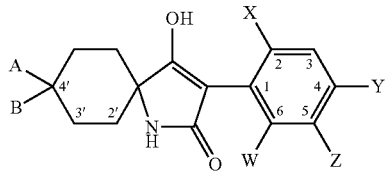

(I-a)

| A | B | X | W | Y | Z |
|---|---|---|---|---|---|
| OCH₃ | CH₃ | C₂H₅ | Br | CH₃ | H |
| OCH₃ | CH₃ | C₂H₅ | Cl | Cl | H |
| OCH₃ | CH₃ | C₂H₅ | Br | Br | H |
| OCH₃ | CH₃ | C₂H₅ | Cl | Br | H |
| OCH₃ | CH₃ | C₂H₅ | Br | Cl | H |
| OCH₃ | CH₃ | OCH₃ | CH₃ | Cl | H |
| OCH₃ | CH₃ | OCH₃ | C₂H₅ | Cl | H |
| OCH₃ | CH₃ | OC₂H₅ | CH₃ | Cl | H |
| OCH₃ | CH₃ | OC₂H₅ | C₂H₅ | Cl | H |
| OCH₃ | CH₃ | Cl | OCH₃ | CH₃ | H |
| OCH₃ | CH₃ | Cl | OC₂H₅ | CH₃ | H |
| OCH₃ | CH₃ | CH₃ | CH₃ | Cl | H |
| OCH₃ | CH₃ | Cl | H | Cl | Cl |
| OCH₃ | CH₃ | CH₃ | H | Cl | CH₃ |
| OCH₃ | CH₃ | Br | H | Cl | CH₃ |
| OCH₃ | CH₃ | Br | H | CH₃ | CH₃ |
| OCH₃ | CH₃ | Cl | H | Br | CH₃ |
| OCH₃ | CH₃ | CH₃ | H | Br | CH₃ |
| OCH₃ | CH₃ | Cl | H | CH₃ | Cl |
| OCH₃ | CH₃ | CH₃ | H | H | CH₃ |
| OCH₃ | CH₃ | Cl | H | H | CH₃ |
| OCH₃ | CH₃ | Br | H | H | CH₃ |
| OCH₃ | CH₃ | CH₃ | H | H | Cl |
| OCH₃ | CH₃ | CH₃ | H | H | Br |
| OCH₃ | CH₃ | CH₃ | CH₃ | CH₃ | CH₃ |
| OCH₃ | CH₃ | CH₃ | CH₃ | CH₃ | F |
| OCH₃ | CH₃ | CH₃ | CH₃ | CH₃ | Cl |
| OCH₃ | CH₃ | CH₃ | CH₃ | CH₃ | Br |
| OCH₃ | CH₃ | CH₃ | CH₃ | H | Cl |
| OCH₃ | CH₃ | CH₃ | CH₃ | H | Br |
| OCH₃ | CH₃ | Cl | Cl | H | Br |
| OCH₃ | CH₃ | CH₃ | CH₃ | 4-Cl—C₆H₄ | H |
| OCH₃ | CH₃ | C₂H₅ | CH₃ | 4-Cl—C₆H₄ | H |
| OCH₃ | CH₃ | C₂H₅ | C₂H₅ | 4-Cl—C₆H₄ | H |
| OCH₃ | CH₃ | Cl | CH₃ | 4-Cl—C₆H₄ | H |
| OCH₃ | CH₃ | Cl | C₂H₅ | 4-Cl—C₆H₄ | H |
| OCH₃ | CH₃ | CH₃ | H | H | 4-Cl—C₆H₄ |
| OCH₃ | CH₃ | CH₃ | CH₃ | H | 4-Cl—C₆H₄ |
| OCH₃ | CH₃ | CH₃ | H | CH₃ | 4-Cl—C₆H₄ |
| OCH₃ | CH₃ | CH₃ | CH₃ | CH₃ | 4-Cl—C₆H₄ |
| OCH₃ | CH₃ | Cl | H | H | H |
| OCH₃ | CH₃ | I | H | H | H |
| OCH₃ | CH₃ | I | H | CH₃ | H |
| OCH₃ | CH₃ | I | CH₃ | H | H |
| OCH₃ | CH₃ | I | C₂H₅ | H | H |
| OCH₃ | CH₃ | CH₃ | H | H | I |
| OCH₃ | CH₃ | CH₃ | H | CH₃ | I |
| OCH₃ | CH₃ | I | H | CH₃ | H |
| OCH₃ | CH₃ | I | C₂H₅ | CH₃ | H |
| OCH₃ | CH₃ | I | CH₃ | Cl | H |
| OCH₃ | CH₃ | I | C₂H₅ | Cl | H |
| OCH₃ | CH₃ | I | Cl | CH₃ | H |
| OCH₃ | CH₃ | I | H | CH₃ | CH₃ |
| OCH₃ | CH₃ | CH₃ | H | I | H |
| OCH₃ | CH₃ | C₂H₅ | H | I | H |
| OCH₃ | CH₃ | CH₃ | CH₃ | I | H |
| OCH₃ | CH₃ | C₂H₅ | CH₃ | I | H |
| OCH₃ | CH₃ | C₂H₅ | C₂H₅ | I | H |
| OCH₃ | CH₃ | Cl | CH₃ | I | H |
| OCH₃ | CH₃ | Cl | C₂H₅ | I | H |
| OCH₃ | CH₃ | CH₃ | H | I | CH₃ |
| OCH₃ | CH₃ | CH₃ | CH₃ | H | I |
| OCH₃ | CH₃ | I | H | H | CH₃ |
| OCH₃ | CH₃ | C₂H₅ | H | H | H |

TABLE 1-continued

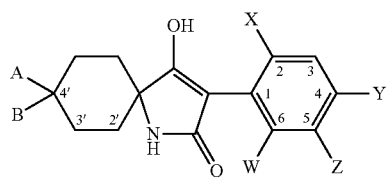

(I-a)

| A | B | X | W | Y | Z |
|---|---|---|---|---|---|
| OCH₃ | CH₃ | △ | H | H | H |
| OCH₃ | CH₃ | △ | CH₃ | H | H |
| OCH₃ | CH₃ | △ | H | CH₃ | H |
| OCH₃ | CH₃ | △ | C₂H₅ | H | H |
| OCH₃ | CH₃ | △ | CH₃ | CH₃ | H |
| OCH₃ | CH₃ | △ | C₂H₅ | CH₃ | H |
| OCH₃ | CH₃ | △ | CH₃ | Cl | H |
| OCH₃ | CH₃ | △ | C₂H₅ | Cl | H |
| OCH₃ | CH₃ | △ | Cl | CH₃ | H |
| OCH₃ | CH₃ | CH₃ | H | △ | H |
| OCH₃ | CH₃ | C₂H₅ | H | △ | H |
| OCH₃ | CH₃ | CH₃ | CH₃ | △ | H |
| OCH₃ | CH₃ | C₂H₅ | CH₃ | △ | H |
| OCH₃ | CH₃ | C₂H₅ | C₂H₅ | △ | H |
| OCH₃ | CH₃ | Cl | CH₃ | △ | H |
| OCH₃ | CH₃ | Cl | C₂H₅ | △ | H |

Furthermore, in addition to the compounds mentioned in the Examples, the following compounds of the formula (I) may be mentioned:

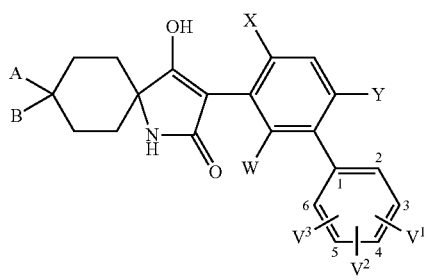

(I)

TABLE 2

| A | B | W | X | Y | $V^1$ | $V^2$ | $V^3$ |
|---|---|---|---|---|---|---|---|
| OCH$_3$ | CH$_3$ | H | Cl | H | 2-F | H | H |
| OCH$_3$ | CH$_3$ | H | Cl | H | 3-F | H | H |
| OCH$_3$ | CH$_3$ | H | Cl | H | 4-F | H | H |
| OCH$_3$ | CH$_3$ | H | Cl | H | 2-F | 4-F | H |
| OCH$_3$ | CH$_3$ | H | Cl | H | 2-F | 4-Cl | H |
| OCH$_3$ | CH$_3$ | H | Cl | H | 2-F | 4-CH$_3$ | H |
| OCH$_3$ | CH$_3$ | H | Cl | H | 2-F | 4-OCH$_3$ | H |
| OCH$_3$ | CH$_3$ | H | Cl | H | 3-F | 4-F | H |
| OCH$_3$ | CH$_3$ | H | Cl | H | 3-F | 4-Cl | H |
| OCH$_3$ | CH$_3$ | H | Cl | H | 3-F | 4-CH$_3$ | H |
| OCH$_3$ | CH$_3$ | H | Cl | H | 3-F | 4-OCH$_3$ | H |
| OCH$_3$ | CH$_3$ | H | Cl | H | 4-F | 3-Cl | H |
| OCH$_3$ | CH$_3$ | H | Cl | H | 4-F | 3-CH$_3$ | H |
| OCH$_3$ | CH$_3$ | H | Cl | H | 4-F | 3-OCH$_3$ | H |
| OCH$_3$ | CH$_3$ | H | Cl | H | 2-F | 4-F | 5-F |
| OCH$_3$ | CH$_3$ | H | Cl | H | 2-F | 4-F | 6-F |
| OCH$_3$ | CH$_3$ | H | Cl | H | 2-F | 4-Cl | 5-F |
| OCH$_3$ | CH$_3$ | H | Cl | H | 2-F | 5-Cl | 4-F |
| OCH$_3$ | CH$_3$ | H | Cl | H | 3-F | 4-F | 5-F |
| OCH$_3$ | CH$_3$ | H | Cl | H | 3-Cl | 4-Cl | H |
| OCH$_3$ | CH$_3$ | H | Cl | H | 4-CF$_3$ | 3-F | H |
| OCH$_3$ | CH$_3$ | H | Cl | H | 4-CN | H | H |
| OCH$_3$ | CH$_3$ | H | Cl | H | 3-CF$_3$ | 4-F | H |
| OCH$_3$ | CH$_3$ | H | CH$_3$ | H | 2-F | H | H |
| OCH$_3$ | CH$_3$ | H | CH$_3$ | H | 3-F | H | H |
| OCH$_3$ | CH$_3$ | H | CH$_3$ | H | 4-F | H | H |
| OCH$_3$ | CH$_3$ | H | CH$_3$ | H | 2-F | 4-F | H |
| OCH$_3$ | CH$_3$ | H | CH$_3$ | H | 2-F | 4-Cl | H |
| OCH$_3$ | CH$_3$ | H | CH$_3$ | H | 2-F | 4-CH$_3$ | H |
| OCH$_3$ | CH$_3$ | H | CH$_3$ | H | 2-F | 4-OCH$_3$ | H |
| OCH$_3$ | CH$_3$ | H | CH$_3$ | H | 3-F | 4-F | H |
| OCH$_3$ | CH$_3$ | H | CH$_3$ | H | 3-F | 4-Cl | H |
| OCH$_3$ | CH$_3$ | H | CH$_3$ | H | 3-F | 4-CH$_3$ | H |
| OCH$_3$ | CH$_3$ | H | CH$_3$ | H | 3-F | 4-OCH$_3$ | H |
| OCH$_3$ | CH$_3$ | H | CH$_3$ | H | 4-F | 3-Cl | H |
| OCH$_3$ | CH$_3$ | H | CH$_3$ | H | 4-F | 3-CH$_3$ | H |
| OCH$_3$ | CH$_3$ | H | CH$_3$ | H | 4-F | 3-OCH$_3$ | H |
| OCH$_3$ | CH$_3$ | H | CH$_3$ | H | 2-F | 4-F | 5-F |
| OCH$_3$ | CH$_3$ | H | CH$_3$ | H | 2-F | 4-F | 6-F |
| OCH$_3$ | CH$_3$ | H | CH$_3$ | H | 2-F | 4-Cl | 5-F |
| OCH$_3$ | CH$_3$ | H | CH$_3$ | H | 2-F | 5-Cl | 4-F |
| OCH$_3$ | CH$_3$ | H | CH$_3$ | H | 3-F | 4-F | 5-F |
| OCH$_3$ | CH$_3$ | H | CH$_3$ | H | 3-Cl | 4-Cl | H |
| OCH$_3$ | CH$_3$ | H | CH$_3$ | H | 4-CF$_3$ | 3-F | H |
| OCH$_3$ | CH$_3$ | H | CH$_3$ | H | 4-CN | H | H |
| OCH$_3$ | CH$_3$ | H | CH$_3$ | H | 3-CF$_3$ | 4-F | H |
| OCH$_3$ | CH$_3$ | CH$_3$ | CH$_3$ | H | 2-F | H | H |
| OCH$_3$ | CH$_3$ | CH$_3$ | CH$_3$ | H | 3-F | H | H |
| OCH$_3$ | CH$_3$ | CH$_3$ | CH$_3$ | H | 4-F | H | H |
| OCH$_3$ | CH$_3$ | CH$_3$ | CH$_3$ | H | 2-F | 4-F | H |
| OCH$_3$ | CH$_3$ | CH$_3$ | CH$_3$ | H | 2-F | 4-Cl | H |
| OCH$_3$ | CH$_3$ | CH$_3$ | CH$_3$ | H | 2-F | 4-CH$_3$ | H |
| OCH$_3$ | CH$_3$ | CH$_3$ | CH$_3$ | H | 2-F | 4-OCH$_3$ | H |
| OCH$_3$ | CH$_3$ | CH$_3$ | CH$_3$ | H | 3-F | 4-F | H |
| OCH$_3$ | CH$_3$ | CH$_3$ | CH$_3$ | H | 3-F | 4-Cl | H |

TABLE 2-continued

| A | B | W | X | Y | $V^1$ | $V^2$ | $V^3$ |
|---|---|---|---|---|---|---|---|
| OCH$_3$ | CH$_3$ | CH$_3$ | CH$_3$ | H | 3-F | 4-CH$_3$ | H |
| OCH$_3$ | CH$_3$ | CH$_3$ | CH$_3$ | H | 3-F | 4-OCH$_3$ | H |
| OCH$_3$ | CH$_3$ | CH$_3$ | CH$_3$ | H | 4-F | 3-Cl | H |
| OCH$_3$ | CH$_3$ | CH$_3$ | CH$_3$ | H | 4-F | 3-CH$_3$ | H |
| OCH$_3$ | CH$_3$ | CH$_3$ | CH$_3$ | H | 4-F | 3-OCH$_3$ | H |
| OCH$_3$ | CH$_3$ | CH$_3$ | CH$_3$ | H | 2-F | 4-F | 5-F |
| OCH$_3$ | CH$_3$ | CH$_3$ | CH$_3$ | H | 2-F | 4-F | 6-F |
| OCH$_3$ | CH$_3$ | CH$_3$ | CH$_3$ | H | 2-F | 4-Cl | 5-F |
| OCH$_3$ | CH$_3$ | CH$_3$ | CH$_3$ | H | 2-F | 5-Cl | 4-F |
| OCH$_3$ | CH$_3$ | CH$_3$ | CH$_3$ | H | 3-F | 4-F | 5-F |
| OCH$_3$ | CH$_3$ | CH$_3$ | CH$_3$ | H | 3-CF$_3$ | 4-F | H |
| OCH$_3$ | CH$_3$ | CH$_3$ | CH$_3$ | H | 3-Cl | 4-Cl | H |
| OCH$_3$ | CH$_3$ | CH$_3$ | CH$_3$ | H | 4-CF$_3$ | 3-F | H |
| OCH$_3$ | CH$_3$ | CH$_3$ | CH$_3$ | H | 4-CN | H | H |
| OCH$_3$ | CH$_3$ | H | CH$_3$ | CH$_3$ | 2-F | H | H |
| OCH$_3$ | CH$_3$ | H | CH$_3$ | CH$_3$ | 3-F | H | H |
| OCH$_3$ | CH$_3$ | H | CH$_3$ | CH$_3$ | 4-F | H | H |
| OCH$_3$ | CH$_3$ | H | CH$_3$ | CH$_3$ | 2-F | 4-F | H |
| OCH$_3$ | CH$_3$ | H | CH$_3$ | CH$_3$ | 2-F | 4-Cl | H |
| OCH$_3$ | CH$_3$ | H | CH$_3$ | CH$_3$ | 2-F | 4-CH$_3$ | H |
| OCH$_3$ | CH$_3$ | H | CH$_3$ | CH$_3$ | 2-F | 4-OCH$_3$ | H |
| OCH$_3$ | CH$_3$ | H | CH$_3$ | CH$_3$ | 3-F | 4-F | H |
| OCH$_3$ | CH$_3$ | H | CH$_3$ | CH$_3$ | 3-F | 4-Cl | H |
| OCH$_3$ | CH$_3$ | H | CH$_3$ | CH$_3$ | 3-F | 4-CH$_3$ | H |
| OCH$_3$ | CH$_3$ | H | CH$_3$ | CH$_3$ | 3-F | 4-OCH$_3$ | H |
| OCH$_3$ | CH$_3$ | H | CH$_3$ | CH$_3$ | 4-F | 3-Cl | H |
| OCH$_3$ | CH$_3$ | H | CH$_3$ | CH$_3$ | 4-F | 3-CH$_3$ | H |
| OCH$_3$ | CH$_3$ | H | CH$_3$ | CH$_3$ | 4-F | 3-OCH$_3$ | H |
| OCH$_3$ | CH$_3$ | H | CH$_3$ | CH$_3$ | 2-F | 4-F | 5-F |
| OCH$_3$ | CH$_3$ | H | CH$_3$ | CH$_3$ | 2-F | 4-F | 6-F |
| OCH$_3$ | CH$_3$ | H | CH$_3$ | CH$_3$ | 2-F | 4-Cl | 5-F |
| OCH$_3$ | CH$_3$ | H | CH$_3$ | CH$_3$ | 2-F | 5-Cl | 4-F |
| OCH$_3$ | CH$_3$ | H | CH$_3$ | CH$_3$ | 3-F | 4-F | 5-F |
| OCH$_3$ | CH$_3$ | CH$_3$ | CH$_3$ | H | 3-Cl | 4-Cl | H |
| OCH$_3$ | CH$_3$ | CH$_3$ | CH$_3$ | H | 4-CF$_3$ | 3-F | H |
| OCH$_3$ | CH$_3$ | CH$_3$ | CH$_3$ | H | 4-CN | H | H |
| OCH$_3$ | CH$_3$ | CH$_3$ | CH$_3$ | H | 3-CF$_3$ | 4-F | H |
| OCH$_3$ | CH$_3$ | CH$_3$ | CH$_3$ | CH$_3$ | 2-F | H | H |
| OCH$_3$ | CH$_3$ | CH$_3$ | CH$_3$ | CH$_3$ | 3-F | H | H |
| OCH$_3$ | CH$_3$ | CH$_3$ | CH$_3$ | CH$_3$ | 4-F | H | H |
| OCH$_3$ | CH$_3$ | CH$_3$ | CH$_3$ | CH$_3$ | 2-F | 4-F | H |
| OCH$_3$ | CH$_3$ | CH$_3$ | CH$_3$ | CH$_3$ | 2-F | 4-Cl | H |
| OCH$_3$ | CH$_3$ | CH$_3$ | CH$_3$ | CH$_3$ | 2-F | 4-CH$_3$ | H |
| OCH$_3$ | CH$_3$ | CH$_3$ | CH$_3$ | CH$_3$ | 2-F | 4-OCH$_3$ | H |
| OCH$_3$ | CH$_3$ | CH$_3$ | CH$_3$ | CH$_3$ | 3-F | 4-F | H |
| OCH$_3$ | CH$_3$ | CH$_3$ | CH$_3$ | CH$_3$ | 3-F | 4-Cl | H |
| OCH$_3$ | CH$_3$ | CH$_3$ | CH$_3$ | CH$_3$ | 3-F | 4-CH$_3$ | H |
| OCH$_3$ | CH$_3$ | CH$_3$ | CH$_3$ | CH$_3$ | 3-F | 4-OCH$_3$ | H |
| OCH$_3$ | CH$_3$ | CH$_3$ | CH$_3$ | CH$_3$ | 4-F | 3-Cl | H |
| OCH$_3$ | CH$_3$ | CH$_3$ | CH$_3$ | CH$_3$ | 4-F | 3-CH$_3$ | H |
| OCH$_3$ | CH$_3$ | CH$_3$ | CH$_3$ | CH$_3$ | 4-F | 3-OCH$_3$ | H |
| OCH$_3$ | CH$_3$ | CH$_3$ | CH$_3$ | CH$_3$ | 2-F | 4-F | 5-F |
| OCH$_3$ | CH$_3$ | CH$_3$ | CH$_3$ | CH$_3$ | 2-F | 4-F | 6-F |
| OCH$_3$ | CH$_3$ | CH$_3$ | CH$_3$ | CH$_3$ | 2-F | 4-Cl | 5-F |
| OCH$_3$ | CH$_3$ | CH$_3$ | CH$_3$ | CH$_3$ | 2-F | 5-Cl | 4-F |
| OCH$_3$ | CH$_3$ | CH$_3$ | CH$_3$ | CH$_3$ | 3-F | 4-F | 5-F |
| OCH$_3$ | CH$_3$ | CH$_3$ | CH$_3$ | H | 3-Cl | 4-Cl | H |
| OCH$_3$ | CH$_3$ | CH$_3$ | CH$_3$ | H | 4-CF$_3$ | 3-F | H |
| OCH$_3$ | CH$_3$ | CH$_3$ | CH$_3$ | H | 4-CN | H | H |
| OCH$_3$ | CH$_3$ | CH$_3$ | CH$_3$ | H | 3-CF$_3$ | 4-F | H |

Table 3 X, W, Y and Z are as indicated in Tables 1 and 2

A=OC$_2$H$_5$;B=CH$_3$

Table 4 X, W, Y and Z are as indicated in Tables 1 and 2

A=OCH$_3$;B=C$_2$H$_5$

In the literature it has already been described how the action of various active compounds can be boosted by addition of ammonium salts. However, these are salts which act as detergents (for example WO 95/017817) or salts having relatively long-chain alkyl and/or aryl substituents which act in a permeabilizing manner or increase the solubility of the active compound (for example EP-A 0 453 086, EP-A 0 664 081, FR-A 2 600 494, U.S. Pat. No. 4,844,734, U.S. Pat. No.

5,462,912, U.S. Pat. No. 5,538,937, US-A 03/0224939, US-A 05/0009880, US-A 05/0096386). Furthermore, the prior art describes the activity only for certain active compounds and/or certain applications of the corresponding compositions. In yet other cases, these are salts of sulphonic acids where the acids for their part have a paralyzing action on insects (U.S. Pat. No. 2,842,476). A boost to action by ammonium sulphate, for example, is described by way of example for the herbicides glyphosate and phosphinothricin and for phenyl-substituted cyclic ketoenols (U.S. Pat. No. 6,645,914, EP-A2 0 036 106, WO 07/068427). A corresponding boost to action for insecticides has already been described in WO 07/068428.

The use of ammonium sulphate as a formulating assistant has also been described for certain active compounds and applications (WO 92/16108), but its purpose therein is to stabilize the formulation, not to boost the action.

It has now likewise been found, surprisingly, that the action of insecticides and/or acaricides and/or herbicides from the class of the geminally alkoxy/alkylspirocyclically substituted tetramic acid derivatives of the formula (I) can be boosted significantly through the addition of ammonium salts or phosphonium salts to the application solution or through the incorporation of these salts into a formulation comprising geminally alkoxy/alkylspirocyclically substituted tetramic acid derivatives of the formula (I). The present invention therefore provides for the use of ammonium salts or phosphonium salts for boosting the action of crop protection compositions which comprise as their active compound herbicidal and/or insecticidal and/or acaricidal geminally alkoxy/alkylspirocyclically substituted tetramic acid derivatives of the formula (I). The invention likewise provides compositions which comprise herbicidal and/or acaricidal and/or insecticidal geminally alkoxy/alkylspirocyclically substituted tetramic acid derivatives of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted plant growth.

The compounds of the formula (I) possess a broad insecticidal and/or acaricidal and/or herbicidal activity, but individually the activity and/or plant tolerance leaves something to be desired.

The active compounds can be used in the compositions of the invention in a broad concentration range. The concentration of the active compounds in the formulation here is usually 0.1-50% by weight.

Formula (III') provides a definition of ammonium salts and phosphonium salts which, according to the invention, boost the activity of crop protection compositions comprising fatty acid biosynthesis inhibitors

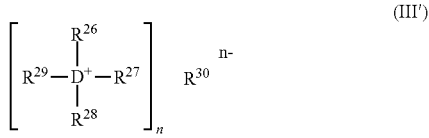

in which
D represents nitrogen or phosphorus,
D preferably represents nitrogen,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano,
$R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl,
$R^{26}$, $R^{27}$, $R^{28}$ and $R^{29}$ very particularly preferably represent hydrogen,
n represents 1, 2, 3 or 4,
n preferably represents 1 or 2,
$R^{30}$ represents an inorganic or organic anion,
$R^{30}$ preferably represents bicarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate,
$R^{30}$ particularly preferably represents lactate, sulphate, nitrate, thiosulphate, thiocyanate, oxalate or formate,
$R^{30}$ very particularly preferably represents sulphate.

Inventively emphasized combinations of active compound, salt and penetrant are listed in the table below. "Penetrant as per test" means here that any compound that acts as a penetrant in the cuticle penetration test (Baur et al., 1997, Pesticide Science 51, 131-152) is suitable.

The ammonium salts and phosphonium salts of the formula (III') can be used in a broad concentration range to boost the activity of crop protection compositions comprising ketoenols. In general, the ammonium salts or phosphonium salts are used in the ready-to-use crop protection composition in a concentration of from 0.5 to 80 mmol/l, preferably 0.75 to 37.5 mmol/l, particularly preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active compound concentration. The concentration of the salt in the formulation here is usually 1-50% by weight.

In one preferred embodiment of the invention, it is not only an ammonium salt and/or phosphonium salt, but additionally a penetrant, that is added to the crop protection compositions to increase the activity. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal and/or acaricidal and/or herbicidal, geminally alkoxy/alkylspirocyclically substituted tetramic acid derivatives of the formula (I) as active compound. The invention likewise provides compositions which comprise herbicidal and/or acaricidal and/or insecticidal geminally alkoxy/alkylspirocyclically substituted tetramic acid derivatives of the formula (I) and penetrants and ammonium salts and/or phosphonium salts, including not only formulated active compounds but also ready-to-use compositions (spray liquors). Finally, the invention also provides the use of these compositions for controlling harmful insects.

Suitable penetrants in the present context are all those substances which are usually used for improving the penetration of agrochemical active compounds into plants. Penetrants are defined in this context by their ability to penetrate from the aqueous spray liquor and/or from the spray coating into the cuticle of the plant and thereby increase the mobility of active compounds in the cuticle. The method described in the literature (Baur et al., 1997, *Pesticide Science* 51, 131-152) can be used for determining this property.

Suitable penetrants are, for example, alkanol alkoxylates. Penetrants according to the invention are alkanol alkoxylates of the formula (IV')

R—O—(-AO—)$_v$—R'  (IV')

in which
R represents straight-chain or branched alkyl having 4 to 20 carbon atoms
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or mixtures of ethylene oxide and propylene oxide radicals or butylene oxide radicals and
v represents a number from 2 to 30.

A preferred group of penetrants are alkanol alkoxylates of the formula

R—O—(-EO—)$_n$—R'  (IV'-a)

in which
R has the meaning given above,
R' has the meaning given above,
EO represents —CH$_2$—CH$_2$—O— and
n represents a number from 2 to 20.

A further preferred group of penetrants are alkanol alkoxylates of the formula

R—O—(-EO—)$_p$—(-PO—)$_q$—R'  (IV'-b)

in which
R has the meaning given above,
R' has the meaning given above,
EO represents —CH$_2$—CH$_2$—O—,
PO represents $$-CH_2-CH(CH_3)-O-,$$

p represents a number from 1 to 10 and
q represents a number from 1 to 10.

A further preferred group of penetrants are alkanol alkoxylates of the formula

R—O—(-PO—)$_r$—(EO—)$_s$—R'  (IV'-c)

in which
R has the meaning given above,
R' has the meaning given above,
EO represents —CH$_2$—CH$_2$—O—,
PO represents $$-CH_2-CH(CH_3)-O-,$$

r represents a number from 1 to 10 and
s represents a number from 1 to 10.

A further preferred group of penetrants are alkanol alkoxylates of the formula

R—O—(-EO—)$_p$—(-BO—)$_q$—R'  (IV'-d)

in which
R and R' have the meanings given above,
EO represents —CH$_2$—CH$_2$—O—,
BO represents $$-CH_2-CH_2-CH(CH_3)-O-,$$

p represents a number from 1 to 10 and
q represents a number from 1 to 10.

A further preferred group of penetrants are alkanol alkoxylates of the formula

R—O—(-BO—)$_r$—(-EO—)$_s$—R'  (IV'-e)

in which
R and R' have the meanings given above,
BO represents $$-CH_2-CH_2-CH(CH_3)-O-,$$

EO represents —CH$_2$—CH$_2$—O—,
r represents a number from 1 to 10 and
s represents a number from 1 to 10.

A further preferred group of penetrants are alkanol alkoxylates of the formula

CH$_3$—(CH$_2$)$_t$—CH$_2$—O—(-CH$_2$—CH$_2$—O—)$_u$—R'  (IV'-f)

in which
R' has the meaning given above,
t represents a number from 8 to 13 and
u represents a number from 6 to 17.

In the formulae given above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV-c), mention may be made of 2-ethylhexyl alkoxylate of the formula CH$_3$—CH$_2$—CH$_2$—CH$_2$—CH(C$_2$H$_5$)—CH$_2$—O—(PO)$_8$—(EO)$_6$—H  (IV'-c-1)

in which
EO represents —CH$_2$—CH$_2$—O—,
PO represents $$-CH_2-CH(CH_3)-O- \text{ and}$$

the numbers 8 and 6 represent average values.

As an example of an alkanol alkoxylate of the formula (IV-d), mention may be made of the formula CH$_3$—(CH$_2$)$_{10}$—O—(-EO—)$_6$—(-BO—)$_2$—CH$_3$  (IV'-d-1)

in which
EO represents —CH$_2$—CH$_2$—O—,
BO represents

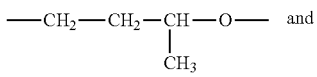

the numbers 10, 6 and 2 represent average values.

Particularly preferred alkanol alkoxylates of the formula (IV'-f) are compounds of this formula in which
t represents a number from 9 to 12 and
u represents a number from 7 to 9.

With very particular preference, mention may be made of alkanol alkoxylate of the formula (IV'-f-1)

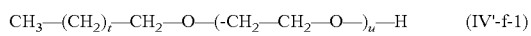

in which
t represents the average value 10.5 and
u represents the average value 8.4.

The above formulae provide general definitions of the alkanol alkoxylates. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, maize seed oil, cottonseed oil and soya bean oil or the esters of said oils. Preference is given to rapeseed oil, sunflower oil and their methyl or ethyl esters.

The concentration of penetrant in the compositions of the invention can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth) acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, in accordance with process (A), for example ethyl N-[(2,4,6-trimethyl)phenylacetyl]-1-amino-4-methoxy-4'-methylcyclohexanecarboxylate as starting material, the course of the process according to the invention can be represented by the following reaction scheme:

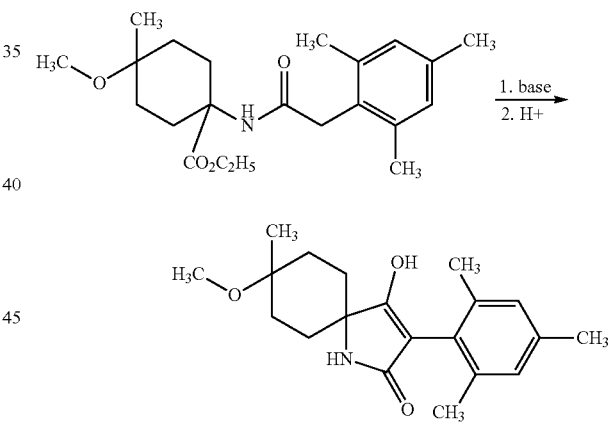

Using, in accordance with process (Bα), for example 8-ethoxy-8'-methyl-3-[(4-chloro-2,6-dimethyl)phenyl]-1-azaspiro[4,5]decane-2,4-dione and pivaloyl chloride as starting materials, the course of the process according to the invention can be represented by the following reaction scheme:

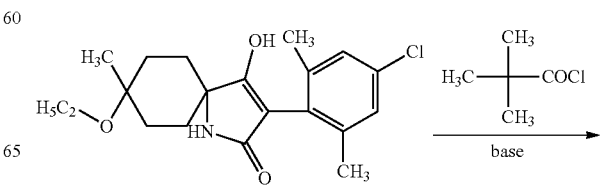

-continued

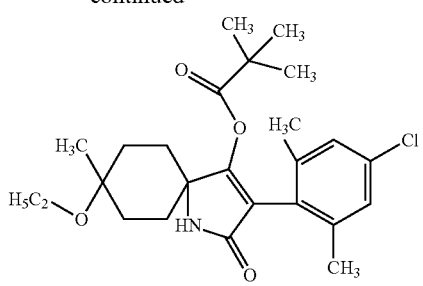

Using, in accordance with process (B) (variant β), for example 8-methoxy-8'-methyl-3-[(2,4-dichloro)phenyl]-1-azaspiro[4,5]decane-2,4-dione and acetic anhydride as starting materials, the course of the process according to the invention can be represented by the following reaction scheme:

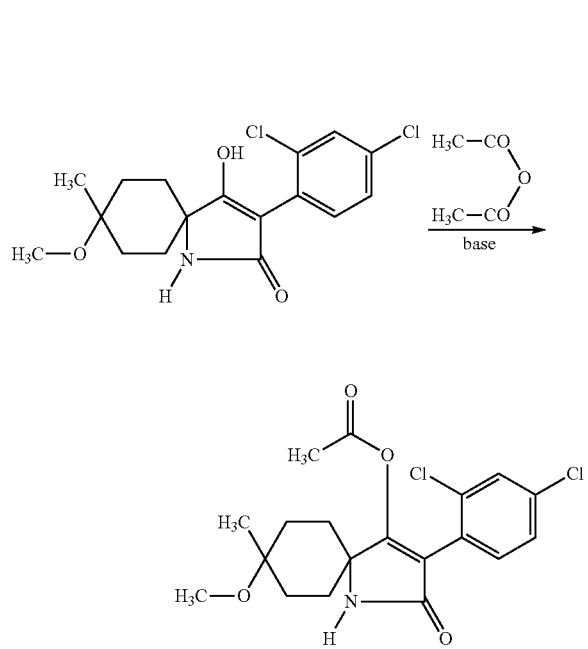

Using, in accordance with process (C), for example 8-methoxy-8'-ethyl-3-[(2,4-dichloro-6-methyl)phenyl]-1-azaspiro[4,5]decane-2,4-dione and ethyl chloroformate as starting materials, the course of the process according to the invention can be represented by the following reaction scheme:

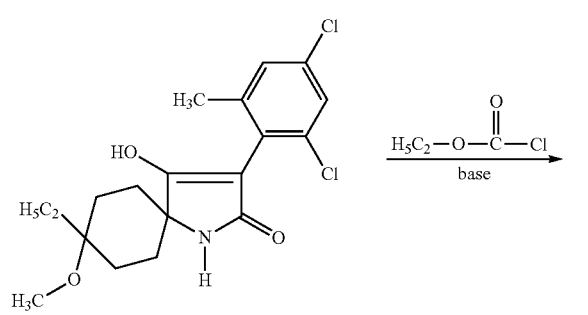

-continued

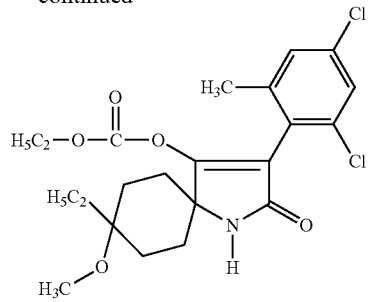

Using, in accordance with process (D), for example 8-ethoxy-8'-methyl-3-[(2,4,6-trimethyl)phenyl]-1-azaspiro[4,5]decane-2,4-dione and methyl chloromonothioformate as starting materials, the the course of the reaction can be represented as follows:

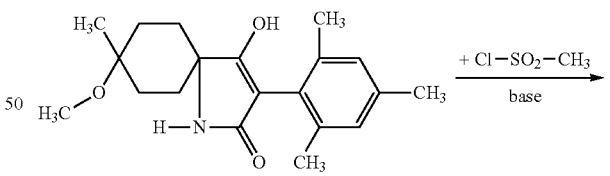

Using, in accordance with process (E), for example 8-methoxy-8'-methyl-3-[(2,4,6-trimethyl)phenyl]-1-azaspiro[4,5]decane-2,4-dione and methanesulphonyl chloride as starting materials, the course of the reaction can be represented by the reaction scheme below:

Using, in accordance with process (F), for example 8-ethoxy-8'-methyl-3-[(2,4-dichloro-6-methyl)-phenyl]-1-azaspiro[4,5]decane-2,4-dione and 2,2,2-trifluoroethyl methanethiophosphonyl chloride as starting materials, the course of the reaction can be represented by the following reaction scheme:

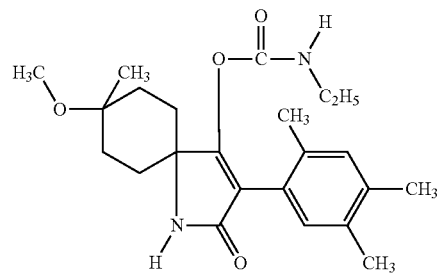

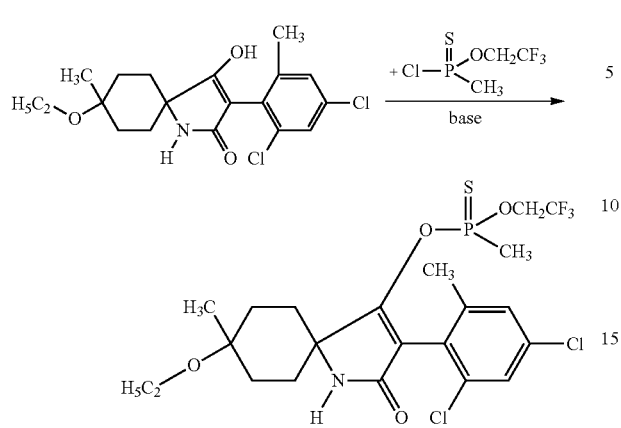

Using, in accordance with process (G), for example 8-methoxy-8'-methyl-3-[(2,3,4,6-tetramethyl-phenyl]-1-azaspiro[4,5]decane-2,4-dione and NaOH as components, the course of the process according to the invention can be represented by the following reaction scheme:

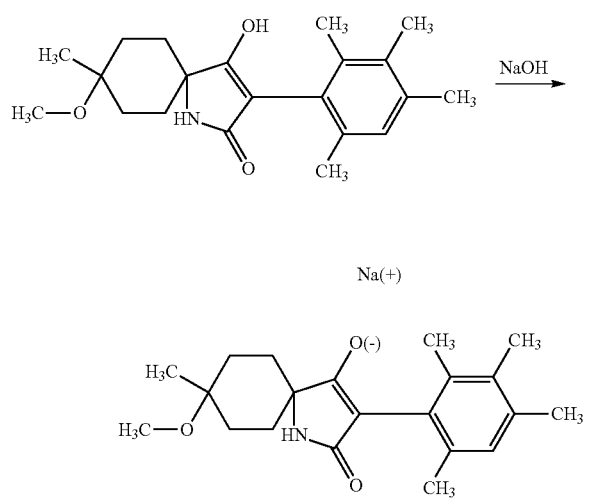

Using, in accordance with process (H) (variant α), for example 8-methoxy-8'-methyl-3-[(2,4,5-trimethyl)phenyl]-1-azaspiro[4,5]decane-2,4-dione and ethyl isocyanate as starting materials, the course of the reaction can be represented by the following reaction scheme:

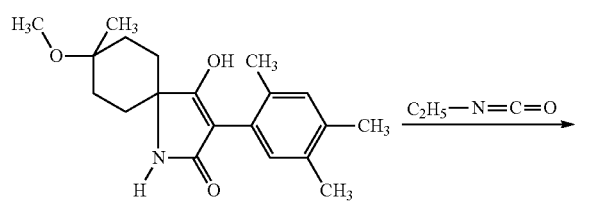

Using, in accordance with process (H) (variant β), for example 8-methoxy-8'-methyl-3-[(2,4,6-trimethyl)phenyl]-1-azaspiro[4,5]decane-2,4-dione and dimethylcarbamoyl chloride as starting materials, the course of the reaction can be represented by the following scheme:

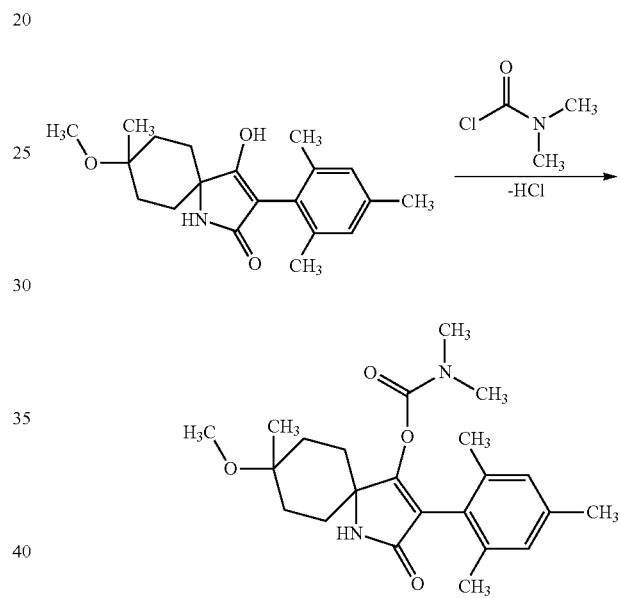

Using, in accordance with process (Iβ), for example 8-methoxy-8'-methyl-3-[(4-bromo-2,6-dimethylphenyl)]-1-azaspiro[4,5]decane-2,4-dione and 4-chlorophenylboronic acid as starting materials, the course of the reaction can be represented by the following scheme:

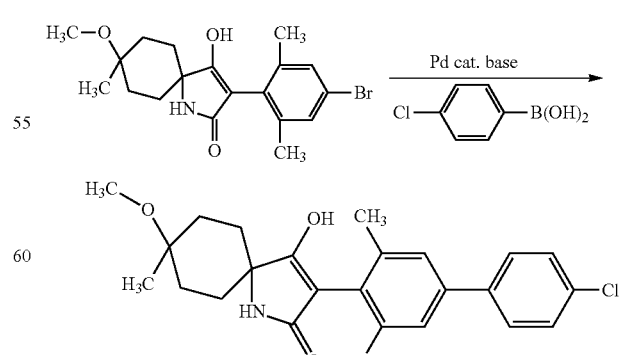

The compounds of the formula (II)

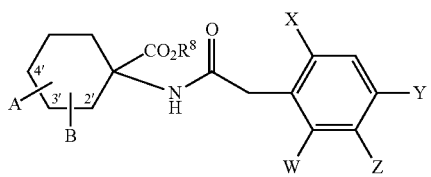
(II)

in which
A, B, W, X, Y, Z and $R^8$ have the meanings given above,
are novel.

The acylamino acid esters of the formula (II) are obtained, for example, when amino acid derivatives of the formula (XIV)

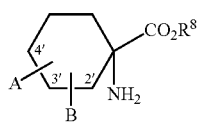
(XIV)

in which
A, B and $R^8$ have the meanings given above,
are acylated with substituted phenylacetic acid derivatives of the formula (XV)

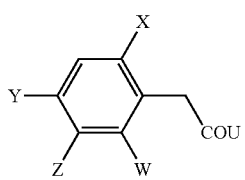
(XV)

in which
W, X, Y and Z have the meanings given above and
U represents a leaving group introduced by reagents for the activation of carboxylic acids, such as carbonyldiimidazole, carbonyldiimides (such as, for example, dicyclohexylcarbodiimide), phosphorylating agents (such as, for example, $POCl_3$, BOP—Cl), halogenating agents, such as, for example, thionyl chloride, oxalyl chloride, phosgene or chloroformic ester
(Chem. Reviews 52, 237-416 (1953); Bhattacharya, Indian J. Chem. 6, 341-5, 1968) or when acylamino acids of the formula (XVI)

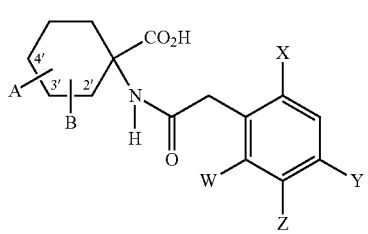
(XVI)

in which
A, B, W, X, Y and Z have the meanings given above,
are esterified (Chem. Ind. (London) 1568 (1968)).

The compounds of the formula (XVI)

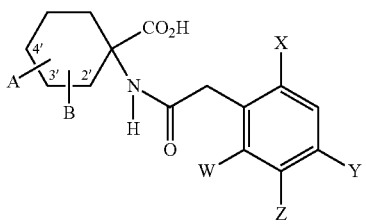
(XVI)

in which
A, B, W, X, Y and Z have the meanings given above,
are novel.

The compounds of the formula (XVI) are obtained, for example, when 1-aminocyclohexanecarboxylic acids of the formula (XVII)

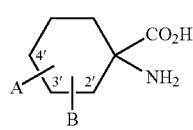
(XVII)

in which
A and B have the meanings given above,
are acylated with substituted phenylacetic acid derivatives of the formula (XV)

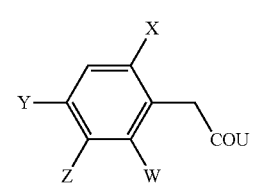
(XV)

in which
U, W, X, Y and Z have the meanings given above, for example following the method of Schotten-Baumann (Organikum [Organic Chemistry], VEB Deutscher Verlag der Wissenschaften, Berlin 1977, p. 505).

Some of the compounds of the formula (XV) are known, and/or they can be prepared by the known processes of the laid-open patents cited at the outset.

The compounds of the formulae (XIV) and (XVII) are novel and can be prepared by known processes (see, for example, Compagnon, Ann. Chim. (Paris) [14] 5, p. 11-22, 23-27 (1970), L. Munday, J. Chem. Soc. 4372 (1961); J. T. Eward, C. Jitrangeri, Can. J. Chem. 53, 3339 (1975).

The novel 1-aminocyclohexanecarboxylic acids (XVII) are generally obtainable by the Bucherer-Bergs synthesis or by the Strecker synthesis and are in each case obtained in different isomer forms. For the sake of simplicity, hereinbelow the isomers in which the oxygen atom in the 4-position and the amino group are positioned equatorial/axial or axial/equatorial are referred to as β. For the sake of simplicity, hereinbelow the isomers in which the amino group and the oxygen atom in the 4-position are equatorial/equatorial or axial/axial are referred to as α.

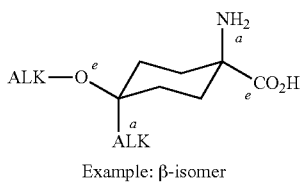

Example: β-isomer

Example: α-isomer

ALK = alkyl (L. Munday, J. Chem. Soc. 4372 (1961)).

The compounds of the formula (XVII) can be obtained from compounds of the formula (XVIII)

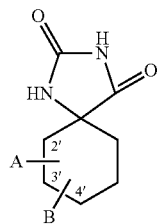

(XVIII)

in which A and B have the meanings given above.

The compounds of the formula (XVIII) are novel and can be prepared by methods known from the literature (for example Bucherer-Bergs reaction, see also the Examples).

Furthermore, the starting materials of the formula (II)

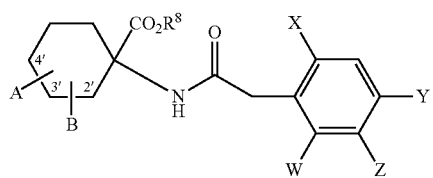

(II)

in which
A, B, W, X, Y, Z and $R^8$ have the meanings given above, can be prepared by reacting 1-aminocyclohexanecarbonitriles of the formula (XIX)

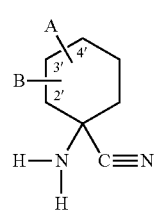

(XIX)

in which
A and B have the meanings given above,
acylating with substituted phenylacetic acid derivatives of the formula (XV)

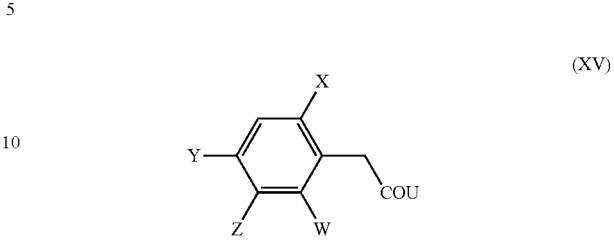

(XV)

in which
U, W, X, Y and Z have the meanings given above,
to give compounds of the formula (XX)

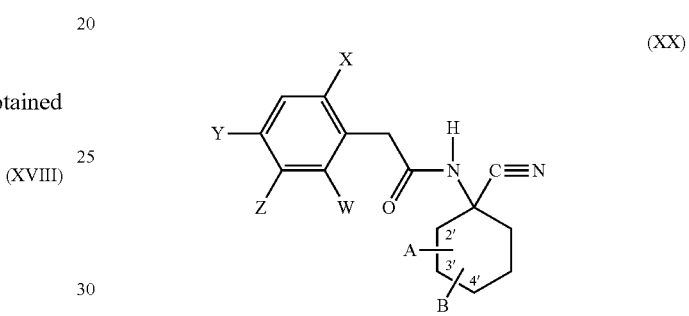

(XX)

in which
A, B, W, X, Y and Z have the meanings given above,
and subsequently subjecting the latter to acid alcoholysis.

The compounds of the formula (XX) are likewise novel, and they can be prepared by known processes of the literature cited at the outset. The compounds of the formula (XIX) are likewise novel, and they can be prepared, for example, as described in EP-A-595 130.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formulae (IX) and (X) and isocyanates of the formula (XI) and carbamoyl chlorides of the formula (XII) and boronic acids of the formula (XIII) furthermore required as starting materials for carrying out the processes (B), (C), (D), (E), (F), (G), (H) and (I) according to the invention are generally known compounds of organic or inorganic chemistry.

The compounds of the formula (XV) are furthermore known from the patent applications cited at the outset, and/or they can be prepared by the methods given therein.

The compounds of the formulae (I-a'-I-g') and (I-a"-I-g") can be prepared by the processes A to H described.

The process (A) is characterized in that compounds of the formula (II) in which A, B, W, X, Y, Z and $R^8$ have the meanings given above are subjected to an intramolecular condensation in the presence of a diluent and in the presence of a base.

Suitable diluents for the process (A) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, isopropanol, butanol, isobutanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA1 (=tris-(methoxyethoxyethyl)-amine). Alkali metals such as sodium or potassium can furthermore be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperature can be varied within a relatively wide range. In general, the process is carried out at temperatures between −75° C. and 200° C., preferably between −50° C. and 150° C. The process (A) according to the invention is generally carried out under atmospheric pressure.

When carrying out the process (A) according to the invention, the reaction component of the formula (II) and the deprotonating base are generally employed in equimolar to approximately double-equimolar amounts. However, it is possible to use one or the other reactants in a larger excess (up to 3 mol).

The process ($B_\alpha$) is characterized in that compounds of the formula (I-a) are in each case reacted with carbonyl halides of the formula (III), if appropriate in the presence of a diluent and if appropriate in the presence of an acid binder.

Suitable diluents for the process ($B_\alpha$) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulphoxide and sulpholane. If the acid halide is sufficiently stable to hydrolysis, the reaction may also be carried out in the presence of water.

Suitable acid binders when carrying out the reaction in accordance with process ($B_\alpha$) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig Base and N,N-dimethylaniline, furthermore alkali metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

The reaction temperature in the process ($B_\alpha$) according to the invention can be varied within a relatively wide range. In general, the process is carried out at temperatures between −20° C. and +150° C., preferably between 0° C. and 100° C.

When carrying out the process ($B_\alpha$) according to the invention, the starting materials of the formula (I-a) and the carbonyl halide of the formula (III) are generally in each case employed in approximately equivalent amounts. However, it is also possible to employ the carboxylic acid halides in a larger excess (of up to 5 mol). Work-up is carried out by customary methods.

The process ($B_\beta$) is characterized in that compounds of the formula (I-a) are in each case reacted with carboxylic anhydrides of the formula (IV), if appropriate in the presence of a diluent and if appropriate in the presence of an acid binder.

Preferred diluents for the process ($B_\beta$) according to the invention are those diluents which are also preferred when acid halides are used. Besides, a carboxylic anhydride used in excess may also simultaneously act as the diluent.

In the process ($B_\beta$), acid binders which are added, if appropriate, are preferably those acid binders which are also preferred when acid halides are used.

In the process ($B_\beta$) according to the invention, the reaction temperature can be varied within a relatively wide range. In general, the process is carried out at temperatures between −20° C. and +150° C., preferably between 0° C. and 100° C.

When carrying out the process ($B_\beta$) according to the invention, the starting materials of the formula (I-a) and the carboxylic anhydride of the formula (IV are generally in each case employed in approximately equivalent amounts. However, it is also possible to employ the carboxylic anhydride in a larger excess (of up to 5 mol). Work-up is carried out by customary methods.

In general, a procedure is followed in which diluent, excess carboxylic anhydride and the carboxylic acid which forms are removed by distillation or by washing with an organic solvent or with water.

The process (C) is characterized in that compounds of the formula (I-a) are in each case reacted with chloroformic esters or chloroformic thioesters of the formula (V), if appropriate in the presence of a diluent and if appropriate in the presence of an acid binder.

Suitable acid binders for the process (C) according to the invention are all customary acid acceptors. Preference is given to using tertiary amines, such as triethylamine, pyridine, DABCO, DBU, DBN, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Diluents which can be employed in process (C) according to the invention are all solvents which are inert to the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethylformamide, dimethyl sulphoxide and sulpholane.

When carrying out the process (C) according to the invention, the reaction temperature can be varied within a relatively wide range. The reaction temperature is generally between −20° C. and +100° C., preferably between 0° C. and 50° C.

Process (C) according to the invention is generally carried out under atmospheric pressure.

When carrying out process (C) according to the invention, the starting materials of the formula (I-a) and the corresponding chloroformic ester or chloroformic thioester of the formula (V) are generally used in each case in approximately equivalent amounts. However, it is also possible to employ one or the other reactant in a larger excess (of up to 2 mol). Work-up is carried out by customary methods. In general, a procedure is followed in which the salts which have precipitated are removed and the reaction mixture which remains is concentrated by stripping off the diluent.

The process (D) according to the invention is characterized in that compounds of the formula (I-a) are in each case reacted with compounds of the formula (VI), in the presence of a diluent and if appropriate in the presence of an acid binder.

In preparation process (D), approximately 1 mol of chloromonothioformic ester or chlorodithioformic ester of the formula (VI) is reacted at from 0 to 120° C., preferably at from 20 to 60° C., per mole of starting compound of the formula (I-a).

Suitable diluents which are added, if appropriate, are all inert polar organic solvents, such as ethers, amides, sulphones, sulphoxides, but also halogenoalkanes.

Preference is given to using dimethyl sulphoxide, tetrahydrofuran, dimethylformamide, ethyl acetate or methylene chloride.

If, in a preferred embodiment, the enolate salt of the compounds (I-a) is prepared by addition of strong deprotonating agents such as, for example, sodium hydride or potassium tertiary-butylate, the further addition of acid binders can be dispensed with.

Suitable bases for the process (D) are all customary proton acceptors. Preference is given to using alkali metal hydrides, alkali metal alkoxides, alkali metal or alkaline earth metal carbonates or bicarbonates or nitrogen bases. Examples which may be mentioned are sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out under atmospheric pressure or under elevated pressure, preferably under atmospheric pressure. Work-up is carried out by customary methods.

The process (E) according to the invention is characterized in that compounds of the formula (I-a) are in each case reacted with sulphonyl chlorides of the formula (VII), if appropriate in the presence of a diluent and if appropriate in the presence of an acid binder.

In the preparation process (E), approximately 1 mol of sulphonyl chloride of the formula (VII) is reacted per mole of starting material of the formula (I-a), at from −20 to 150° C., preferably from 0 to 70° C.

The process (E) is preferably carried out in the presence of a diluent.

Suitable diluents are all inert polar organic solvents, such as ethers, amides, ketones, carboxylic esters, nitriles, sulphones, sulphoxides or halogenated hydrocarbons, such as methylene chloride.

Preference is given to using dimethyl sulphoxide, tetrahydrofuran, dimethylformamide, ethyl acetate or methylene chloride.

If, in a preferred embodiment, the enolate salt of the compound (I-a) is prepared by addition of strong deprotonating agents (such as, for example, sodium hydride or potassium tert-butoxide), the further addition of acid binders can be dispensed with.

If acid binders are employed, these are customary inorganic or organic bases, for example sodium hydroxide, sodium carbonate, potassium carbonate, pyridine and triethylamine.

The reaction can be carried out under atmospheric pressure or under elevated pressure, preferably under atmospheric pressure. Work-up is carried out by customary methods.

The process (F) according to the invention is characterized in that compounds of the formula (I-a) are in each case reacted with phosphorus compounds of the formula (VIII), if appropriate in the presence of a diluent and if appropriate in the presence of an acid binder.

In preparation process (F), 1 to 2, preferably 1 to 1.3, mol of the phosphorus compound of the formula (VIII) are reacted at temperatures of between −40° C. and 150° C., preferably between −10 and 110° C., per mole of the compounds (I-a) in order to obtain compounds of the formula (I-e).

The process (F) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Substances which are preferably employed are acetonitrile, dimethyl sulphoxide, tetrahydrofuran, dimethylformamide, methylene chloride.

Suitable acid binders which are optionally added are customary inorganic or organic bases such as hydroxides, carbonates or amines. Examples include sodium hydroxide, sodium carbonate, potassium carbonate, pyridine and triethylamine.

The reaction can be carried out under atmospheric pressure or under elevated pressure, preferably under atmospheric pressure. Work-up is carried out by customary methods of organic chemistry. The end products are preferably purified by crystallization, chromatographic purification or "incipient distillation", i.e. removal of the volatile components under reduced pressure.

The process (G) is characterized in that compounds of the formula (I-a) are in each case reacted with metal hydroxides or metal alkoxides of the formula (IX) or amines of the formula (X), if appropriate in the presence of a diluent.

Preferred diluents for the process (G) according to the invention are ethers, such as tetrahydrofuran, dioxane, diethyl ether, or else alcohols, such as methanol, ethanol, isopropanol, but also water. Process (G) according to the invention is generally carried out under atmospheric pressure. The reaction temperature is generally between −20° C. and 100° C., preferably between 0° C. and 50° C.

The process (H) according to the invention is characterized in that compounds of the formula (I-a) are in each case reacted with (Hα) compounds of the formula (XI), if appropriate in the presence of a diluent and if appropriate in the presence of a catalyst, or (Hβ) with compounds of the formula (XII), if appropriate in the presence of a diluent and if appropriate in the presence of an acid binder.

In the preparation process (Hα), approximately 1 mol of isocyanate of the formula (XI) is reacted per mole of starting material of the formula (I-a), at from 0 to 100° C., preferably at from 20 to 50° C.

The process (Hα) is preferably carried out in the presence of a diluent.

Suitable diluents are all inert organic solvents, such as aromatic hydrocarbons, halogenated hydrocarbons, ethers, amides, nitriles, sulphones or sulphoxides.

If appropriate, catalysts may be added to accelerate the reaction. Catalysts which can be employed very advantageously are organotin compounds such as, for example, dibutyltin dilaurate.

The process is preferably carried out under atmospheric pressure.

In the preparation process (Hβ), approximately 1 mol of carbamoyl chloride of the formula (XII) is reacted per mole of starting material of the formula (I-a), at from 0 to 150° C., preferably from 20 to 70° C.

Suitable diluents which are added, if appropriate, are all inert polar organic solvents, such as ethers, carboxylic esters, nitriles, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents (such as, for example, sodium hydride or potassium tert-butoxide), the further addition of acid binders can be dispensed with.

If acid binders are employed, these are customary inorganic or organic bases, for example sodium hydroxide, sodium carbonate, potassium carbonate triethylamine or pyridine.

The reaction can be carried out under atmospheric pressure or under elevated pressure, preferably under atmospheric pressure. Work-up is carried out by customary methods.

Suitable catalysts for carrying out the process (Iα) and (Iβ) according to the invention are palladium(0) complexes. Preference is given, for example, to tetrakis(triphenylphosphine)palladium. If appropriate, it is also possible to use palladium (II) compounds, for example $PdCl_2$, $Pd(OAc)_2$. If palladium (II) compounds are used, phosphines, such as, for example, tricyclohexylphosphine, are generally employed as complex formers.

Suitable acid acceptors for carrying out the process (Iα) and (Iβ) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate, caesium carbonate or ammonium carbonate, sodium bicarbonate or potassium bicarbonate, alkali metal fluorides, such as, for example, caesium fluoride, alkali metal phosphates, such as, for example, potassium dihydrogen phosphate, potassium phosphate and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (Iα) and (Iβ) according to the invention are water, organic solvents and any mixtures thereof. Those which may be mentioned by way of example are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethyl glycol monomethyl ether; water.

In the process (Iα) and (Iβ) according to the invention, the reaction temperature can be varied within a relatively wide range. In general, the process is carried out at temperatures between 0° C. and +140° C., preferably between 50° C. and +100° C.

When carrying out the process (Iα) and (Iβ) according to the invention, the boronic acids of the formulae (XIIIα) and (XIIIβ) in which Y and Z have the meaning given above and compounds of the formulae (I-a') to (I-g') in which A, B, G, W, X, Y and Z' have the meaning given above or compounds of the formulae (I-a'') to (I-g'') in which A, B, G, W, X, Z and Y' have the meaning given above are employed in a molar ratio of from 1:1 to 3:1, preferably from 1:1 to 2:1. In general, from 0.005 to 0.5 mol, preferably from 0.01 mol to 0.1 mol, of catalyst are employed per mole of the compounds of the formulae (I-a') to (I-g') or (I-a'') to (I-g''). The base is generally employed in excess. Work-up is carried out by customary methods.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha*

*elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*.

It is furthermore possible to control Protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus* and *Porcellio scaber*.

From the order of the Isoptera, for example, *Acromyrmex* spp., *Atta* spp., *Maizeitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolle-* tis spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp, *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp. and *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms). If appropriate, they can also be used as intermediates or precursors for the synthesis of other active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, that is, liquid solvents, and/or solid carriers, optionally with the use of surfactants, that is to say emulsifiers and/or dispersants, and/or foam-formers. The formulations are prepared either in suitable plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, a carrier is a natural or synthetic, organic or inorganic substance which may be solid or liquid and with which the active compounds are mixed or bonded for better applicability, in particular for application to plants or plant parts. The solid or liquid carrier is generally inert and should be suitable for use in agriculture.

Suitable solid carriers are:
for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are non-ionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus possible are, for example, reduced application rates and/or a widening of the activity spectrum and/or an increase of the activity of the compounds and compositions used according to the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processibility of the harvested products, which exceed the effects normally to be expected.

The transgenic plants or plant cultivars (i.e. those obtained by genetical engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasised examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetables, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasised are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasised are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed it the future.

The plants stated can be treated particularly advantageously in accordance with the invention with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly *larvae*, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Railietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

It has furthermore been found that the compounds according to the invention also have a strong insecticidal action against insects which destroy industrial materials.

The following insects may be mentioned as examples and as preferred—but without a limitation:

Beetles, such as *Hylotrupes bajulus, Chlorophorus pilosis, Anobium punctatum, Xestobium rufovillosum, Ptilinus pectimaizeis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec.

*Apate monachus, Bostrychus capucins, Heterobostrychus brunneus, Sinoxylon* spec. *Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

The ready-to-use compositions can also comprise other insecticides, if appropriate, and also one or more fungicides, if appropriate.

With respect to additional partners for mixing, reference is made to the insecticides and fungicides mentioned above.

The compounds according to the invention can at the same time be employed for protecting objects which come into contact with saltwater or brackish water, such as hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia griseila, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The compounds of the formula (I) according to the invention (active compounds) have excellent herbicidal activity against a broad spectrum of economically important mono- and dicotyledonous annual harmful plants. The active compounds act efficiently even on perennial weeds which produce shoots from rhizomes, root stocks and other perennial organs and which are difficult to control.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulphate or ammonium thiocyanate.

The novel active compound combinations can be used as such, in the form of their formulations or in the use forms prepared therefrom by further dilution, such as ready-to-use solutions, suspensions, emulsions, powders, pastes and granules. They are used in a customary manner, for example by watering, spraying, atomizing, dusting or broadcasting.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), maize, soya beans, potatoes, cotton, oilseed rape, beet, sugar cane and also fruit plants (with the fruits apples, pears, citrus fruits and grapevines), greater emphasis being given to cereals, maize, soya beans, potatoes, cotton and oilseed rape.

The active compounds according to the invention can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the nenera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants stated can be treated particularly advantageously in accordance with the invention with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza,*

*Panicum, Saccharum, Secale, Sorghum, Triticale, Triticum, Zea*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus possible are, for example, reduced application rates and/or a widening of the activity spectrum and/or an increase of the activity of the compounds and compositions used according to the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processibility of the harvested products, which exceed the effects normally to be expected.

Owing to their herbicidal and plant-growth-regulatory properties, the active compounds can also be employed for controlling harmful plants in crops of known genetically modified plants or genetically modified plants still to be developed. In general, the transgenic plants are distinguished by special advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition. Other particular properties may be tolerance or resistance to abiotic stressors, for example heat, low temperatures, drought, salinity and ultraviolet radiation.

It is preferred to use the compounds of the formula (I) according to the invention in economically important transgenic crops of useful plants and ornamentals, for example of cereals such as wheat, barley, rye, oats, sorghum and millet, rice, cassava and maize or else crops of sugar beet, cotton, soya bean, oilseed rape, potato, tomato, peas and other vegetables.

It is preferred to employ the compounds of the formula (I) as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

recombinant modifications of crop plants for the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulphonylurea type (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg or Christou, "Trends in Plant Science" 1 (1996) 423-431.

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulphonylureas, glyphosate, glufosinate or benzoylisoxazoles and analogous active compounds.

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc, N.Y. 1964; Schonfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleylmethyltauride. To prepare the wettable powders, the herbicidally active compounds are ground finely, for example, in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The term "active compounds" or "compounds" always also includes the active compound combinations mentioned here.

The preparation and the use of the active compounds according to the invention is illustrated by the examples below.

PREPARATION EXAMPLES

Example I-a-1, I-a-2

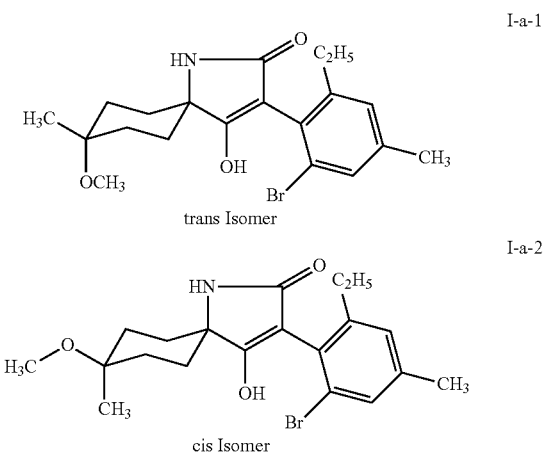

0.46 g (4.1 mmol) of potassium tert-butoxide is initially charged in 4 ml of N,N-dimethylacetamide (DMA). At 20° C., 0.6 g (1.36 mmol) of the compound according to Example II-7 in 10 ml of DMA is added dropwise, and the mixture is stirred for 2 h. The reaction mixture is poured onto ice-water, acidified with dilute hydrochloric acid and extracted with methylene chloride, and the extract is dried and concentrated. The residue is chromatographed on silica gel using methylene chloride/ethyl acetate 3:1. This gives 0.09 g (15% of theory) of the compound I-a-1 of m.p. 219° C. and 0.1 g (16% of theory) of the compound I-a-2 of m.p. 178° C.

$^1$H-NMR (400 MHz, d$_6$-DMSO): shift δ in ppm

Trans Isomer 1.03 (t, 3H, CH$_2$—C$\underline{H}_3$), 1.09 (s, 3H, CH$_3$), 1.05-1.24 (m, 2H, CH$_2$), 1.60-1.68 (m, 2H, CH$_2$), 1.74-1.78 (m, 2H, CH$_2$), 2.04-2.12 (m, 2H, CH$_2$), 2.28 (s, 3H, Ar—C$\underline{H}_3$), 2.40-2.46 (m, 2H, Ar—C$\underline{H}_2$—CH$_3$), 3.10 (s, 3H, OCH$_3$), 7.02 (s, 1H, Ar—H), 7.26 (s, 1H, Ar—H), 7.82 (s, br, 1H, NH), 10.52 (s, 1H, OH).

Cis Isomer 1.03 (t, 3H, CH$_2$—C$\underline{H}_3$), 1.18 (s, 3H, CH$_3$), 1.47-1.58 (m, 2H, CH$_2$), 1.66-1.93 (m, 6H, C$\underline{H}_2$), 2.28 (s, 3H, Ar—CH$_3$), 2.40-2.46 (m, 2H, Ar—C$\underline{H}_2$CH$_3$), 3.15 (s, 3H, OCH$_3$), 7.02 (s, 1H, Ar—H), 7.26 (s, 1H, Ar—H), 7.72 (s, br, 1H, NH), 10.53 (s, 1H, OH).

The following compounds of the formula (I-a) are obtained analogously to Examples (I-a-1) and (I-a-2) and following the general preparation instructions

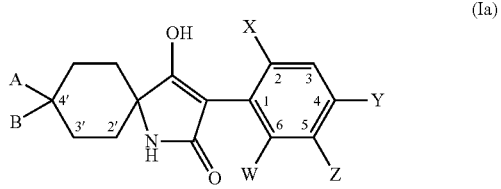

| Ex. No. | W | X | Y | Z | A | B | m.p. C | Isomer |
|---|---|---|---|---|---|---|---|---|
| I-a-3 | CH$_3$ | CH$_3$ | Cl | H | OCH$_3$ | CH$_3$ | 286 | cis/trans about 1:5 |
| I-a-4 | CH$_3$ | CH$_3$ | Br | H | OCH$_3$ | CH$_3$ | 308 | trans |
| I-a-5 | CH$_3$ | Cl | Cl | H | OCH$_3$ | CH$_3$ | 312 | trans |
| I-a-6 | H | CH$_3$ | H | CH$_3$ | OCH$_3$ | CH$_3$ | 100 | trans |
| I-a-7 | CH$_3$ | OCH$_3$ | Cl | H | OCH$_3$ | CH$_3$ | 239 | cis/trans about 1:4 |
| I-a-8 | C$_2$H$_5$ | OCH$_3$ | Cl | H | OCH$_3$ | CH$_3$ | 237 | trans |
| I-a-9 | C$_2$H$_5$ | OCH$_3$ | Cl | H | OCH$_3$ | CH$_3$ | 239 | cis/trans about 4:1 |
| I-a-10 | CH$_3$ | CH$_3$ | H | 4-Cl—Ph | OCH$_3$ | CH$_3$ | 254 | trans |
| I-a-11 | CH$_3$ | CH$_3$ | H | 4-F—Ph | OCH$_3$ | CH$_3$ | 265 | trans |
| I-a-12 | CH$_3$ | CH$_3$ | CH$_3$ | H | OCH$_3$ | CH$_3$ | 259 | trans |
| I-a-13 | CH$_3$ | OCH$_3$ | Cl | H | OC$_2$H$_5$ | CH$_3$ | 216 | trans |
| I-a-14 | CH$_3$ | OCH$_3$ | Cl | H | OC$_2$H$_5$ | CH$_3$ | 108 | cis |
| I-a-15 | H | CH$_3$ | H | 4-F—Ph | OCH$_3$ | CH$_3$ | 143 | trans |
| I-a-16 | CH$_3$ | CH$_3$ | H | Br | OCH$_3$ | CH$_3$ | 241 | trans |
| I-a-17 | CH$_3$ | CH$_3$ | Cl | H | OC$_2$H$_5$ | CH$_3$ | 260 | trans |
| I-a-18 | CH$_3$ | CH$_3$ | H | 4-F—Ph | OC$_2$H$_5$ | CH$_3$ | 142 | cis |
| I-a-19 | CH$_3$ | CH$_3$ | H | 4-F—Ph | OCH$_3$ | CH$_3$ | 276 | trans |
| I-a-20 | CH$_3$ | CH$_3$ | Cl | H | OCH$_3$ | CH$_3$ | 273 | trans |
| I-a-21 | CH$_3$ | CH$_3$ | Cl | H | OCH$_3$ | CH$_3$ | 258 | cis |
| I-a-22 | CH$_3$ | CH$_3$ | CH$_3$ | H | OC$_2$H$_5$ | CH$_3$ | 140 | trans |
| I-a-23 | CH$_3$ | CH$_3$ | CH$_3$ | H | OC$_2$H$_5$ | CH$_3$ | 1) | cis |
| I-a-24 | C$_2$H$_5$ | OCH$_3$ | Cl | H | OCH$_3$ | C$_2$H$_5$ | 2) | cis |
| I-a-25 | C$_2$H$_5$ | OCH$_3$ | Cl | H | OCH$_3$ | C$_2$H$_5$ | 218 | trans |
| I-a-26 | CH$_3$ | CH$_3$ | CH$_3$ | H | OCH$_3$ | C$_2$H$_5$ | 251 | trans |
| I-a-27 | CH$_3$ | CH$_3$ | Br | H | OCH$_3$ | C$_2$H$_5$ | 185 | trans |
| I-a-28 | CH$_3$ | CH$_3$ | Cl | H | OCH$_3$ | C$_2$H$_5$ | 230 | cis |
| I-a-29 | CH$_3$ | CH$_3$ | Cl | H | OCH$_3$ | C$_2$H$_5$ | decomposition | trans |
| I-a-30 | CH$_3$ | CH$_3$ | H | 4-F—Ph | OCH$_3$ | C$_2$H$_5$ | decomposition | cis |
| I-a-31 | CH$_3$ | CH$_3$ | H | 4-F—Ph | OCH$_3$ | C$_2$H$_5$ | decomposition | trans |
| I-a-32 | C$_2$H$_5$ | OCH$_3$ | Cl | H | OCH$_3$ | C$_2$H$_5$ | 92 | cis |
| I-a-33 | C$_2$H$_5$ | OCH$_3$ | Cl | H | OCH$_3$ | C$_2$H$_5$ | 96 | trans |
| I-a-34 | CH$_3$ | CH$_3$ | H | 4-Cl—Ph | OCH$_3$ | C$_2$H$_5$ | 159 | trans |
| I-a-35 | CH$_3$ | OCH$_3$ | Cl | H | OCH$_3$ | C$_2$H$_5$ | 243 | trans |
| I-a-36 | CH$_3$ | OCH$_3$ | Cl | H | OCH$_3$ | C$_2$H$_5$ | wax | cis |
| I-a-37 | C$_2$H$_5$ | Br | CH$_3$ | H | OCH$_3$ | C$_2$H$_5$ | 3) | trans |
| I-a-38 | CH$_3$ | OCH$_3$ | CH$_3$ | H | OCH$_3$ | CH$_3$ | 212 | trans/cis 18:1 |
| I-a-39 | CH$_3$ | OCH$_3$ | CH$_3$ | H | OCH$_3$ | CH$_3$ | 300 | trans/cis 1:2 |
| I-a-40 | CH$_3$ | Br | Cl | H | OCH$_3$ | CH$_3$ | 294 | cis |
| I-a-41 | CH$_3$ | Cl | Br | H | OCH$_3$ | CH$_3$ | 319 | cis |
| I-a-42 | C$_2$H$_5$ | OC$_2$H$_5$ | Cl | H | OCH$_3$ | CH$_3$ | 178 | trans |
| I-a-43 | H | CH$_3$ | Cl | H | OCH$_3$ | CH$_3$ | 219 | cis |
| I-a-44 | H | Cl | Cl | H | OCH$_3$ | CH$_3$ | 312 | cis |
| I-a-45 | C$_2$H$_5$ | C$_2$H$_5$ | CH$_3$ | H | OCH$_3$ | CH$_3$ | 254 | trans |
| I-a-46 | CH$_3$ | Br | Cl | H | OCH$_3$ | CH$_3$ | 304 | trans |
| I-a-47 | CH$_3$ | Cl | Br | H | OCH$_3$ | CH$_3$ | 324 | trans |
| I-a-48 | CH$_3$ | C$_2$H$_5$ | Br | H | OCH$_3$ | CH$_3$ | 274 | trans |
| I-a-49 | CH$_3$ | C$_2$H$_5$ | Br | H | OCH$_3$ | CH$_3$ | 281 | cis |
| I-a-50 | H | CH$_3$ | Cl | H | OCH$_3$ | CH$_3$ | 245 | trans |
| I-a-51 | H | Cl | Cl | H | OCH$_3$ | CH$_3$ | 238 | trans |
| I-a-52 | CH$_3$ | Cl | 4-Cl—Ph | H | OCH$_3$ | CH$_3$ | 293 | trans |
| I-a-53 | CH$_3$ | Cl | 4-Cl—Ph | H | OCH$_3$ | CH$_3$ | 302 | cis |
| I-a-54 | CH$_3$ | CH$_3$ | 4-Cl—Ph | H | OCH$_3$ | CH$_3$ | 237 | trans |
| I-a-55 | CH$_3$ | OC$_2$H$_5$ | Cl | H | OCH$_3$ | CH$_3$ | 4) | trans |
| I-a-56 | CH$_3$ | CH$_3$ | Br | H | OC$_2$H$_5$ | CH$_3$ | 5) | cis/trans about 7:1 |
| I-a-57 | CH$_3$ | CH$_3$ | Br | H | OC$_2$H$_5$ | CH$_3$ | 6) | trans |
| I-a-58 | C$_2$H$_5$ | OCH$_3$ | Cl | H | OC$_2$H$_5$ | CH$_3$ | 91 | cis/trans mixture |
| I-a-59 | C$_2$H$_5$ | Br | CH$_3$ | H | OC$_2$H$_5$ | CH$_3$ | 115 | cis/trans mixture |
| I-a-60 | CH$_3$ | CH$_3$ | 4-Cl—Ph | H | OC$_2$H$_5$ | CH$_3$ | 251 | trans/cis approx. |
| I-a-61 | CH$_3$ | CH$_3$ | 4-Cl—Ph | H | OC$_2$H$_5$ | CH$_3$ | 185-195 | cis/trans approx. |
| I-a-62 | C$_2$H$_5$ | Br | CH$_3$ | H | OCH$_3$ | C$_2$H$_5$ | 122 | trans |
| I-a-63 | CH$_3$ | C$_2$H$_5$ | CH$_3$ | H | OCH$_3$ | C$_2$H$_5$ | 254-255 | trans |
| I-a-64 | CH$_3$ | C$_2$H$_5$ | CH$_3$ | H | OCH$_3$ | C$_2$H$_5$ | 81 | cis/trans about 2:1 |

-continued

| Ex. No. | W | X | Y | Z | A | B | m.p. C | Isomer |
|---|---|---|---|---|---|---|---|---|
| I-a-65 | $CH_3$ | $C_2H_5$ | Br | H | $OCH_3$ | $C_2H_5$ | 250-252 | trans |
| I-a-66 | $CH_3$ | $C_2H_5$ | Br | H | $OCH_3$ | $C_2H_5$ | 76 | cis |
| I-a-67 | H | $CH_3$ | H | 4-F—Ph | $OCH_3$ | $C_2H_5$ | 115-117 | trans |
| I-a-68 | $CH_3$ | $OCH_3$ | $CH_3$ | H | $OCH_3$ | $C_2H_5$ | 216-219 | trans |
| I-a-69 | $C_2H_5$ | $C_2H_5$ | $CH_3$ | H | $OCH_3$ | $C_2H_5$ | 7) | cis |
| I-a-70 | $CH_3$ | $CH_3$ | H | 4-F—Ph | $OCH_3$ | $C_3H_7$ | 8) | cis |
| I-a-71 | $CH_3$ | $CH_3$ | H | 4-F—Ph | $OCH_3$ | $C_3H_7$ | 9) | trans |

Ph = phenyl

[1] H-NMR (400 MHz, $d_6$-DMSO): shift δ in ppm

[1)] 1.09 (tr, 3H, $CH_2\underline{CH_3}$), 1.46-1.50 (cm, 2H), 2.04 (s, 6H, 2xAr$CH_3$), 2.22 (s, 3H, Ar-4-$CH_3$), 3.44 (q, 2H, O$\underline{CH_2}CH_3$)

[2)] 0.77 (t, 3H, $CH_2\underline{CH_3}$), 1.00 (tr, 3H, $CH_2\underline{CH_3}$), 2.43 (dq, 2H, $\overline{Ar—CH_2}CH_3$), 3.66 (s 3H, Ar$\underline{OCH_3}$)

[3)] 0.85 (t, 3H, $CH_2\underline{CH_3}$), 1.03 (t, 3H, Ar—$\overline{CH_2}$—$CH_3$), 1.11-1.14 (dm, 1H, $CH_2$), 1.21-1.24 (dm, 1H, $CH_2$), 1.41-1.47 (q, 2H, $\underline{CH_2}$—$\overline{CH_3}$), 2.28 (s, 3H, Ar—$CH_3$), 2.$\overline{40}$-$\overline{2}$.46 (dq, 2H, Ar—$\underline{CH_2}CH_3$), 7.02 (s, 1H, Ar—H), 7.26 (s, 1H, Ar—H), $\overline{7.84}$ (s, br, 1H, NH), 10.52 (s, 1H, OH)

[4)] 1.07 (s, 3H, $CH_3$), 1.20 (t, 3H, $OCH_2\underline{CH_3}$), 2.09 (s, 3H, Ar—$CH_3$), 3.87-3.94 (m, 2H, O—$\underline{CH_2}$—$CH_3$)

[5)] 1.09 (t, 3H, $CH_2$—$\underline{CH_3}$), 1.20 (s, 3$\overline{H}$, $CH_3$), 2.08 (s, 6H, Ar—$CH_3$), 3.41-3.46 (q, 2H, O$\underline{CH_2}$—$CH_3$), 7.21 (s, 2H, Ar—H), 7.8 (s, br, 1$\overline{H, NH}$)

[6)] 1.10 (s, 3H, $CH_3$), 1.10 (t, 3H, $CH_2\underline{CH_3}$), 2.08 (s, 6H, Ar—$CH_3$), 3.3-3.35 (q, 2H, O$\underline{CH_2}CH_3$), 7.2 (s, 2H, Ar—H), 7.88 (s, br, 1H—NH)

[7)] 0.79 (t, 3H, $CH_2$—$\underline{CH_3}$), 1.02 (t, 6H, Ar—$CH_2$—$CH_3$), 1.56-1.62 (q, 2H, $\underline{CH_2}$—$CH_3$), 2.26 (s, 3H, Ar—$CH_3$), 2.33-2.37 (q, 4H, Ar—$\overline{CH_2}$—$CH_3$), 3.10 (s, 3H, $OCH_3$), 6.84 (s, 2H, Ar—H), $\overline{7.72}$ (s, br, 1H, NH)

[8)] 0.92 (t, 3H, $CH_2$—$\underline{CH_3}$), 1.97, 2.12 (2s, 6H, Ar—$CH_3$), 3.10 (s, 3H, $OCH_3$), 7.03-7.05 (d, 1H, Ar—H), 7.10-7.12 (d, 1H, Ar—H), 7.25-7.$\overline{32}$ (m, 4H, Ar—H), 8.03 (s, br, 1H, NH)

[9)] 0.90 (t, 3H, $CH_2$—$\underline{CH_3}$), 1.97, 2.12 (2s, 6H, Ar—$CH_3$), 3.05 (s, 3H, $OCH_3$), 7.03-7.05 (d, 1H, Ar—H), 7.10-7.12 (d, 1H, Ar—H), 7.12-7.$\overline{32}$ (m, 4H, Ar—H), 8.11 (s, br, 1H, NH).

Example I-b-1

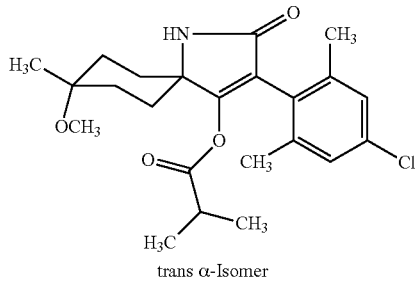 [SMILES: COC1(C)CCC2(CC1)NC(=O)C(c1c(C)cc(Cl)cc1C)=C2OC(=O)C(C)C]

trans α-Isomer 0.525 g (1.5 mmol) of the compound according to Example (I-a-3) is initially charged in 20 ml of ethyl acetate (EA), and 0.21 ml (1.5 mmol) of triethylamine and 10 mg of 4-N,N-dimethylaminopyridine are added. Under reflux, 0.16 ml (1.5 mmol) of isobutyryl chloride in 1.5 ml of EA is added dropwise, and the mixture is stirred for 2 h. After cooling, the mixture is concentrated and the residue is chromatographed on silica gel using methylene chloride/ethyl acetate 10:1. This gives 0.45 g (71% of theory) of melting point 236° C.

[1] H-NMR (400 MHz, $d_6$-DMSO), shift δ in ppm 0.94-0.96 (d, 6H, CH($\underline{CH_3}$)$_2$), 1.09 (s, 3H, $CH_3$), 1.21-1.23 (dm, 2H, $CH_2$), 1.62-1.63 (tm, 2H, $CH_2$), 1.77-1.79 (dm, 2H, $CH_2$), 1.91-1.97 (tm, 2H, $CH_2$), 2.11 (s, 6H, Ar$CH_3$), 2.62-2.65 (m, 1H, $\underline{CH}(CH_3)_2$), 3.07 (s, 3H, $OCH_3$), 7.13 (s, 2H, Ar—H), 9.04 (s, br, 1H, NH).

The following compounds of the formula (I-b) are obtained analogously to Example (I-b-1) and following the general preparation instructions

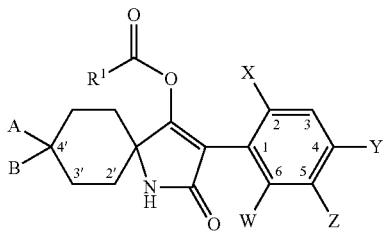

(I-1-b)

| Ex. No. | W | X | Y | Z | A | B | R1 | m.p. C | Isomer |
|---|---|---|---|---|---|---|---|---|---|
| I-b-2 | $CH_3$ | $CH_3$ | Br | H | $OCH_3$ | $C_2H_5$ | i-$C_3H_7$ | 228 | trans |

Example I-c-1

525 mg (1.5 mmol) of the compound according to Example (I-a-3) are initially charged in 20 ml of dichloromethane, and 0.21 ml (1.5 mmol) of triethylamine and 10 mg of 4-N,N-dimethylaminopyridine are added. At room temperature, 0.14 ml (1.5 mmol) of ethyl chloroformate in 1 ml of dichloromethane is added dropwise, and the mixture is stirred for 1 h. The solvent is evaporated and the residue is chromatographed on silica gel using methylene chloride/ethyl acetate 10:1.

Yield: 0.35 g (54% of theory) of melting point 238° C.

$^1$H-NMR (400 MHz, CD$_3$CN); shift δ in ppm:

1.06 (t, 3H, CH$_2$CH$_3$), 1.15 (s, 3H, CH$_3$), 1.34-1.39 (d, m, 2H, CH$_2$), 1.50-1.58 (dt, 2H, CH$_2$), 2.05-2.12 (dt, 2H, CH$_2$), 3.15 (s, 3H, OCH$_3$), 3.98-4.03 (q, 2H, OCH$_2$CH$_3$), 7.10 (s, 2H, Ar—H), 7.3 (s, br, 1H, NH).

The following compounds of the formula (I-c) are obtained analogously to Example (I-c-1) and following the general preparation instructions:

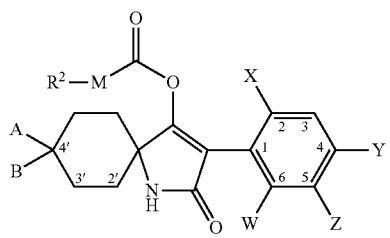
(I-c)

| Ex. No. | W | X | Y | Z | A | B | M | R2 | m.p. C | Isomer |
|---|---|---|---|---|---|---|---|---|---|---|
| I-1-c-2 | CH$_3$ | CH$_3$ | CH$_3$ | H | OCH$_3$ | CH$_3$ | O | C$_2$H$_5$ | 178-182 | trans |
| I-1-c-2 | CH$_3$ | CH$_3$ | CH$_3$ | H | OCH$_3$ | CH$_3$ | O | C$_2$H$_5$ | 205-211 | cis |
| I-1-c-2 | CH$_3$ | CH$_3$ | Br | H | OCH$_3$ | C$_2$H$_5$ | O | C$_2$H$_5$ | 234 | trans |

Example II-1

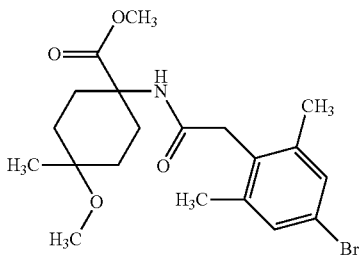 [SMILES: COC(=O)C1(NC(=O)Cc2c(C)cc(Br)cc2C)CCC(C)(OC)CC1]

5.23 g (22 mmol) of the compound according to Example (XIV-1) are initially charged in 80 ml of tetrahydrofuran (THF), and 6.1 ml (44 mmol) of triethylamine are added. With rapid stirring, 5.23 g (20 mmol) of 4-bromo-2,6-dimethylphenylacetyl chloride dissolved in 10 ml of THF are then added at 20° C. After 4 h of stirring at 40° C., the mixture is concentrated and the residue is chromatographed on silica gel using a gradient of methyl chloride+0→10% ethyl acetate.

Yield: 4.3 g (36% of theory), m.p. 158° C.

$^1$H-NMR (400 MHz, CD$_3$CN): δ=1.08, 1.10 (2s, 3H, CH$_3$), 2.25, 2.27 (2s, 6H, ArCH$_3$), 3.11, 3.13 (2s, 3H, OCH$_3$), 3.50-3.57 (ms, 5H, CO$_2$CH$_3$, COCH$_2$), 7.20, 7.21 (2s, 2H, ArH) ppm.

The following compounds of the formula (II) are obtained analogously to Example (II-1) and following the general preparation instructions. The isomers are enriched using chromatographic methods, preferably on silica gel.

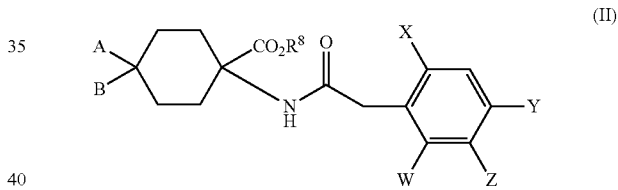
(II)

| Ex. No. | W | X | Y | Z | A | B | R8 | m.p. C | Isomer |
|---|---|---|---|---|---|---|---|---|---|
| II-2 | CH$_3$ | CH$_3$ | Cl | H | OCH$_3$ | CH$_3$ | CH$_3$ | 150 | mixture |
| II-3 | H | CH$_3$ | H | CH$_3$ | OCH$_3$ | CH$_3$ | CH$_3$ | 119 | mixture |
| II-4 | C$_2$H$_5$ | Br | CH$_3$ | H | OCH$_3$ | CH$_3$ | CH$_3$ | 152 | cis/trans about 1:4 |
| II-5 | CH$_3$ | Cl | Cl | H | OCH$_3$ | CH$_3$ | CH$_3$ | 144 | mixture |
| II-6 | CH$_3$ | CH$_3$ | CH$_3$ | H | OCH$_3$ | CH$_3$ | CH$_3$ | 135 | mixture |
| II-7 | C$_2$H$_5$ | Br | CH$_3$ | H | OCH$_3$ | CH$_3$ | CH$_3$ | wax | cis/trans about 13:5 |
| II-8 | CH$_3$ | CH$_3$ | Cl | H | OCH$_3$ | CH$_3$ | CH$_3$ | 147 | cis |
| II-9 | CH$_3$ | CH$_3$ | H | 4-Cl—Ph | OCH$_3$ | CH$_3$ | CH$_3$ | wax | cis/trans about 1:4 |
| II-10 | H | CH$_3$ | H | 4-F—Ph | OCH$_3$ | CH$_3$ | CH$_3$ | 148 | mixture |
| II-11 | CH$_3$ | CH$_3$ | H | 4-F—Ph | OCH$_3$ | CH$_3$ | CH$_3$ | wax | mixture |
| II-12 | CH$_3$ | OCH$_3$ | Cl | H | OC$_2$H$_5$ | CH$_3$ | CH$_3$ | 137 | mixture |
| II-13 | CH$_3$ | OCH$_3$ | Cl | H | OCH$_3$ | CH$_3$ | CH$_3$ | wax | cis/trans about 1:2 |
| II-14 | C$_2$H$_5$ | OCH$_3$ | Cl | H | OCH$_3$ | CH$_3$ | CH$_3$ | 163 | mixture |
| II-15 | CH$_3$ | CH$_3$ | H | 4-F—Ph | OC$_2$H$_5$ | CH$_3$ | CH$_3$ | wax | mixture |
| II-16 | CH$_3$ | CH$_3$ | CH$_3$ | H | OC$_2$H$_5$ | CH$_3$ | CH$_3$ | 121 | cis/trans about 4:9 |
| II-17 | CH$_3$ | CH$_3$ | Cl | H | OC$_2$H$_5$ | CH$_3$ | CH$_3$ | 145 | mixture |
| II-18 | C$_2$H$_5$ | OCH$_3$ | Cl | H | OCH$_3$ | C$_2$H$_5$ | CH$_3$ | 122 | cis |
| II-19 | C$_2$H$_5$ | OCH$_3$ | Cl | H | OCH$_3$ | C$_2$H$_5$ | CH$_3$ | wax | trans |
| II-20 | CH$_3$ | OCH$_3$ | Cl | H | OCH$_3$ | C$_2$H$_5$ | CH$_3$ | 171 | mixture |
| II-21 | CH$_3$ | CH$_3$ | Cl | H | OCH$_3$ | C$_2$H$_5$ | CH$_3$ | 188 | mixture |

-continued

| Ex. No. | W | X | Y | Z | A | B | R8 | m.p. C | Isomer |
|---|---|---|---|---|---|---|---|---|---|
| II-22 | $C_2H_5$ | $OC_2H_5$ | Cl | H | $OCH_3$ | $C_2H_5$ | $CH_3$ | 170 | mixture |
| II-23 | $CH_3$ | $CH_3$ | $CH_3$ | H | $OCH_3$ | $C_2H_5$ | $CH_3$ | 164 | mixture |
| II-24 | $CH_3$ | $CH_3$ | Br | H | $OCH_3$ | $C_2H_5$ | $CH_3$ | 196 | mixture |
| II-25 | $CH_3$ | $CH_3$ | H | 4-Cl—Ph | $OCH_3$ | $C_2H_5$ | $CH_3$ | 109 | cis/trans about 1:4 |
| II-26 | $CH_3$ | $CH_3$ | H | 4-F—Ph | $OCH_3$ | $C_2H_5$ | $CH_3$ | wax | cis/trans about 1:10 |
| II-27 | $C_2H_5$ | Br | $CH_3$ | H | $OCH_3$ | $C_2H_5$ | $CH_3$ | 181 | trans |
| II-28 | $CH_3$ | $CH_3$ | Cl | H | $OCH_3$ | $CH_3$ | $CH_3$ | 1) | trans |
| II-29 | $CH_3$ | $OCH_3$ | $CH_3$ | H | $OCH_3$ | $CH_3$ | $CH_3$ | 160 | mixture |
| II-30 | $CH_3$ | Cl | Br | H | $OCH_3$ | $CH_3$ | $CH_3$ | 156 | mixture |
| II-31 | $CH_3$ | Br | Cl | H | $OCH_3$ | $CH_3$ | $CH_3$ | 166 | mixture |
| II-32 | $CH_3$ | $C_2H_5$ | Br | H | $OCH_3$ | $CH_3$ | $CH_3$ | 150 | mixture |
| II-33 | $C_2H_5$ | $C_2H_5$ | $CH_3$ | H | $OCH_3$ | $CH_3$ | $CH_3$ | 136 | mixture |
| II-34 | $C_2H_5$ | $OC_2H_5$ | Cl | H | $OCH_3$ | $CH_3$ | $CH_3$ | 167 | mixture |
| II-35 | H | $CH_3$ | Cl | H | $OCH_3$ | $CH_3$ | $CH_3$ | 134 | mixture |
| II-36 | H | Cl | Cl | H | $OCH_3$ | $CH_3$ | $CH_3$ | 149 | mixture |
| II-37 | $C_2H_5$ | Br | $CH_3$ | H | $OC_2H_5$ | $CH_3$ | $CH_3$ | 129-130 | mixture cis/trans about 3:5 |
| II-38 | $CH_3$ | $CH_3$ | H | 4-Cl—Ph | $OC_2H_5$ | $CH_3$ | $CH_3$ | wax | mixture cis/trans about 3:4 |
| II-39 | $CH_3$ | $CH_3$ | Br | H | $OC_2H_5$ | $CH_3$ | $CH_3$ | 154-155 | mixture cis/trans about 1:3 |
| II-40 | $CH_3$ | $OC_2H_5$ | Cl | H | $OCH_3$ | $CH_3$ | $CH_3$ | wax | mixture |
| II-42 | $CH_3$ | $OCH_3$ | Cl | H | $OC_2H_5$ | $CH_3$ | $CH_3$ | wax | mixture |
| II-43 | $C_2H_5$ | Br | $CH_3$ | H | $OCH_3$ | $C_2H_5$ | $CH_3$ | wax | trans |
| II-44 | $CH_3$ | $OCH_3$ | $CH_3$ | H | $OCH_3$ | $C_2H_5$ | $CH_3$ | 149-151 | mixture |
| II-45 | H | $CH_3$ | H | 4-F—Ph | $OCH_3$ | $C_2H_5$ | $CH_3$ | 60-62 | mixture |
| II-46 | $CH_3$ | $C_2H_5$ | Br | H | $OCH_3$ | $C_2H_5$ | $CH_3$ | 183 | mixture |
| II-47 | $CH_3$ | $C_2H_5$ | $CH_3$ | H | $OCH_3$ | $C_2H_5$ | $CH_3$ | wax | mixture |
| II-48 | $C_2H_5$ | $C_2H_5$ | $CH_3$ | H | $OCH_3$ | $C_2H_5$ | $CH_3$ | 166-168 | mixture |
| II-49 | $CH_3$ | $CH_3$ | H | 4-F—Ph | $OCH_3$ | $C_3H_7$ | $CH_3$ | wax | mixture |

1) $^1$H-NMR (400 MHz, CD3CN): shift δ in ppm: 1.09 (s, 3H, $CH_3$), 1.34-1.42 (tm, 2H, $CH_2$), 2.27 (s, 6H, AR—$CH_3$), 3.11 (s, 3H, $OCH_3$), 3.56 (s, 5H, $CH_2$—C(=O), $CO_2CH_3$),
6.56 (s, br, 1H, NH), 7.07 (s, 2H, Ar—H)

Example XIV-1

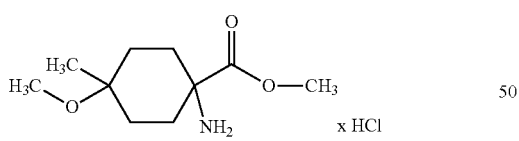

At 0 to 5° C. and under argon, 7.2 g (32 mmol) of the compound from Ex. XVII-1 are initially charged in 150 ml of methanol. 10 ml of thionyl chloride are added dropwise, and the mixture is stirred at 0° C. for 30 minutes and at 40° C. for 24 h until a clear solution is formed. The mixture is then cooled to 5° C., and the precipitate is filtered off with suction. The solution is concentrated using a rotary evaporator and the residue is crystallized using methylene chloride/hexane.

Yield: 5.9 g (76% of theory)

$^1$H-NMR (400 MHz, $d_6$-DMSO): δ=1.07, 1.10 (2s, 3H, $CH_3$), 3.08, 3.09 (2s, 3H, $OCH_3$), 3.75, 3.76 (s, 3H, $CO_2CH_3$) ppm.

Example XVII-1

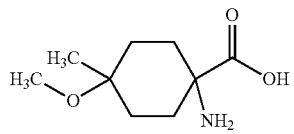

Under argon, 6.85 g of the compound according to Example XVIII-1 are suspended in 80 ml of 30% strength KOH and stirred under reflux overnight.

The mixture is concentrated to about 25% of its original volume using a rotary evaporator and, at 0-10° C., adjusted to pH 2 with conc. HCl. The solution is concentrated using a rotary evaporator and dried. The residue is directly esterified to XIV-1.

Example XVIII-1

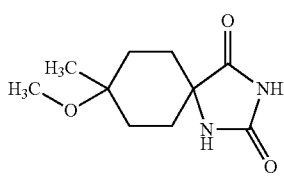

Ammonium carbonate (27 g) and sodium cyanide (2.92 g) are initially charged in 120 ml of water. Starting at room temperature 7.7 g of 4-methoxy-4-methylcyclohexanone are added dropwise, and the reaction mixture is stirred at 55° C. to 60° C. for four hours, concentrated to 50 ml, then stirred at 0° to 5° C. for two hours and filtered off with suction at about −2° C., and the product is washed with a little ice-water and dried.

Yield: 6.9 g (52% of theory) cis/trans isomer mixture about 1:2 according to NMR, $^1$H-NMR (400 MHz, $d_6$-DMSO): δ=1.06, 1.11 (2s, 3H, C$\underline{H}_3$), 3.08, 3.10 (2s, 3H, OC$\underline{H}_3$), 7.86, 8.21 (s, br, 1H, N$\underline{H}$).

Preparation of 4-Methoxy-4-Methylcyclohexanone
(According to Wulff, D et al, Synthesis 1999, 415-422)

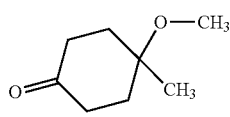
C

In a 600 ml beaker, 9 ml of conc. HCl are added to 8.9 g of the compound B in 50 ml of THF and 70 ml of water. The mixture is stirred at 20° C. for 2 hours and neutralized with 20% strength NaOH to pH 7. The mixture is concentrated using a rotary evaporator and extracted with methyl tert-butyl ether/water; and the organic phase is washed with saturated NaCl solution, dried and concentrated using a rotary evaporator.

This gives 7.7 g (=82.7% of theory) of 4-methoxy-4-methylcyclohexanone in a purity of 62% according to GC/MS, which is used without further purification directly for the synthesis of (XXI-1).

Preparation of B

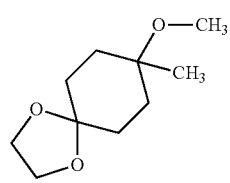
B

In a 100 ml three-necked flask and under argon, 3.5 g of sodium hydride are stirred 3× with 20 ml of hexane pa. (the hexane is removed using a pipette). 20 ml of THF are added. At 20° C., 7.6 g of compound A in 80 ml of THF are added dropwise, the mixture is stirred at 20° C. for 30 minutes and 11 ml of methyl iodide and 1.65 g of tetramethylammonium bromide are then added rapidly.

The mixture is stirred at 20° C. overnight. At 0° C., 10 ml of isopropanol are slowly added dropwise. The mixture is extracted with methyl tert-butyl ether/water and the organic phase is washed with saturated NaCl solution, dried and concentrated using a rotary evaporator. This gives 9 g (=80% of theory) of a purity of 73% according to GC/MS. Without further purification, the product is deketalized with hydrochloric acid to give C.

Preparation of A

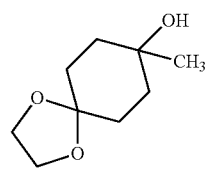
C

Under argon, 1000 ml of toluene and 1000 ml of 1 molar methylmagnesium bromide solution in THF are initially charged in a 4000 ml three-necked flask. At from 0 to 5° C., 156.2 g of 1,4-cyclohexanedione monoethylene glycol ketal in 130 ml of THF are added dropwise over 2 hours. The mixture is stirred at from 0 to 5° C. for 4 hours, and 200 ml of NH$_4$Cl solution are then added. The phases are separated, the aqueous phase is extracted with CH$_2$Cl$_2$ and the organic phases are dried with MgSO$_4$.

The solvent is distilled off at atmospheric pressure and the residue is distilled at 1 mbar/110-115° C. using a 10 cm Vigreux column.

This gives 152.3 g (=88% of theory).

Example 1

1. Herbicidal Pre-Emergence Action

Seeds of monocotyledonous and dicotyledonous weed and crop plants are placed in sandy loam in wood fibre pots and covered with soil. The test compounds, formulated in the form of wettable powders (WP), are then, as an aqueous suspension with a water application rate of 600 l/ha (converted), with 0.2% of wetting agent added, applied at various dosages to the surface of the covering soil.

After the treatment, the pots are placed in a greenhouse and kept under good growth conditions for the test plants. The visual assessment of the damage to the test plants is carried out after a trial period of 3 weeks by comparison with untreated controls (herbicidal activity in percent: 100% activity=the plants have died, 0% activity=like control plants).

In addition to the compounds mentioned above, the following compounds show an activity of ≥80% against *Echinocloa crus-galli*, *Lolium multiflorum* and *Setaria viridis* when applied by the pre-emergence method at 320 g/ha of a.i.: I-a-1, I-a-2, I-a-7, I-a-8, I-a-9, I-a-10, I-a-24, I-a-25, I-a-32, I-a-33, I-a-37, I-a-41, I-a-48, I-a-49, I-a-52, I-a-53, I-a-54, I-a-58, I-a-59, I-a-63, I-a-64, I-a-66, I-a-69

2. Herbicidal Post-Emergence Action

Seeds of monocotyledonous and dicotyledonous weed and crop plants are placed in sandy loam in wood fibre pots, covered with soil and cultivated in a greenhouse under good growth conditions. 2 to 3 weeks after sowing, the test plants are treated at the one-leaf stage. The test compounds, formulated as wettable powders (WP), are then, with a water application rate of 600 l/ha (converted), with 0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (herbicidal activity in percent: 100% activity=the plants have died, 0% activity=like control plants).

In addition to the compounds mentioned above, the following compounds show an activity of ≥80% against *Alopecurus myosuroides*, *Echinocloa crus-galli*, *Lolium multiflorum* and *Setaria viridis* when applied by the post-emergence method at 80 g/ha: I-a-1, I-a-2, I-a-9, I-a-22, I-a-25, I-a-32, I-a-33, I-a-37, I-a-38, I-a-41, I-a-42, I-a-45, I-a-48, I-a-49, I-a-58, I-a-59, I-a-62, I-a-63, I-a-64, I-a-69.

Use of Safeners:

If it is additionally to be tested as to whether safeners can improve the plant compatibility of test substances in the case of crop plants, the following options are used for applying the safener:

- seeds of the crop plants are, before sowing, dressed with the safener substance (the amount of safener stated in percent, based on the weight of the seed)
- before application of the test substances, the crop plants are sprayed with the safener at a certain application rate per hectare (usually 1 day before the application of the test substances)
- the safener is applied together with the test substance as a tank mix (the amount of safener stated in g/ha or as a ratio, based on the herbicide).

Container Trials with Cereal in a Greenhouse

Mefenpyr 1 Day Prior to Herbicide Application

TABLE 1

| | Application rate g a.i./ha | 10 days after application Summer barley observed (%) | Application rate g a.i./ha | 10 days after application Summer wheat observed (%) |
|---|---|---|---|---|
| (I-a-2) | 100 | 30 | 100 | 60 |
| | 50 | 10 | 50 | 60 |
| | | | 25 | 50 |
| | | | 12.5 | 30 |
| (I-a-2) + mefenpyr | 100 + 50 | 2 | 100 + 50 | 30 |
| | 50 + 50 | 2 | 50 + 50 | 10 |
| | | | 25 + 50 | 5 |
| | | | 12.5 + 50 | 3 |

TABLE 2

| | Application rate g a.i./ha | 28 days after application Summer barley observed (%) | Application rate g a.i./ha | 10 days after application Summer wheat observed (%) |
|---|---|---|---|---|
| (I-a-9) | 100 | 50 | 100 | 30 |
| | 50 | 20 | 50 | 30 |
| | | | 25 | 20 |
| (I-a-9) + mefenpyr | 100 + 50 | 8 | 100 + 50 | 10 |
| | 50 + 50 | 5 | 50 + 50 | 10 |
| | | | 25 + 50 | 5 |

TABLE 3

| | Application rate g a.i./ha | 10 days after application Summer wheat observed (%) | 28 days after application Summer wheat observed (%) |
|---|---|---|---|
| I-a-2 | 100 | 50 | 60 |
| | 50 | 50 | 60 |
| | 25 | 40 | 30 |
| | 12.5 | 40 | 10 |
| (I-a-2) + mefenpyr | 100 + 50 | 20 | 5 |
| | 50 + 50 | 10 | 2 |
| | 25 + 50 | 8 | 0 |
| | 12.5 + 50 | 5 | 0 |

TABLE 4

| | Application rate g a.i./ha | 10 days after application Summer barley observed (%) | 10 days after application Summer wheat observed (%) |
|---|---|---|---|
| I-a-49 | 100 | 70 | 50 |
| | 50 | 50 | 50 |
| | 25 | 50 | 50 |
| | 12.5 | 40 | 40 |
| (I-a-49) + mefenpyr | 100 + 50 | 40 | 30 |
| | 50 + 50 | 20 | 30 |
| | 25 + 50 | 20 | 20 |
| | 12.5 + 50 | 5 | 20 |

TABLE 5

| | Application rate g a.i./ha | 28 days after application Summer wheat observed (%) |
|---|---|---|
| (I-a-64) | 50 | 70 |
| | 25 | 60 |
| | 12.5 | 20 |
| (I-a-64) + mefenpyr | 50 + 50 | 20 |
| | 25 + 50 | 10 |
| | 12.5 + 50 | 0 |

TABLE 6

| | Application rate g a.i./ha | 28 days after application Summer barley observed (%) | 10 days after application Summer wheat observed (%) |
|---|---|---|---|
| (I-a-69) | 100 | 15 | 40 |
| | 50 | 10 | 40 |
| | 25 | 10 | 30 |
| | 12.5 | | 20 |
| (I-a-69) + mefenpyr | 100 + 50 | 5 | 15 |
| | 50 + 50 | 3 | 15 |
| | 25 + 50 | 0 | 10 |
| | 12.5 + 50 | | 10 |

Example 2

*Phaedon* Test (PHAECO Spray Treatment)

Solvent: 78.0 parts by weight of acetone
  1.5 parts by weight of dimethylformamide
Emulsifier: 0.5 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with *larvae* of the mustard beetle (*Phaedon cochleariae*).

After the desired period of time, the effect in % is determined. 100% means that all beetle *larvae* have been killed; 0% means that none of the beetle *larvae* have been killed.

In this test, for example, the following compounds of the Preparation Examples show, at an application rate of 500 g/ha, an effect of ≥80%:

Ex. No. I-a-3, I-a-4, I-a-5, I-a-10, I-a-15, I-a-12, I-a-14, I-a-13, I-a-17, I-a-19, I-a-18, I-a-26, I-a-20, I-a-22, I-a-27, I-a-28, I-a-29, I-a-34, I-a-36, I-a-38, I-a-39, I-a-47, I-a-49, I-a-50, I-a-51, I-a-63, I-a-64

Example 3

*Spodoptera frugiperda* Test (SPODFR Spray Treatment)

Solvent: 78.0 parts by weight of acetone
1.5 parts by weight of dimethylformamide
Emulsifier: 0.5 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show, at an application rate of 500 g/ha, an effect of ≥0.80%:

Ex. No. 1-a-10, I-a-15, 1-a-34, 1-a-61, I-a-71, I-c-2

Example 4

*Myzus persicae* Test (MYZUPE Spray Treatment)

Solvent: 78.0 parts by weight of acetone
1.5 parts by weight of dimethylformamide
Emulsifier: 0.5 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (*Brassica pekinensis*) infested by all stages of the green peach aphid (*Myzus persicae*) are sprayed with an active compound preparation of the desired concentration.

After the desired period of time, the effect in % is determined. 100% means that all of the aphids have been destroyed; 0% means that none of the aphids have been destroyed.

In this test, for example, the following compounds of the Preparation Examples show, at an application rate of 500 g/ha, an effect of ≥280%:

Ex. No. I-a-3, I-a-4, I-a-5, I-a-6, I-a-7, I-a-8, I-a-9, I-a-2, I-a-1, I-a-10, I-a-11, I-a-15, I-a-12, I-a-14, I-a-13, I-a-16, I-a-17, I-a-19, I-a-18, I-a-24, I-a-20, I-a-21, I-a-22, I-a-23, I-a-26, I-a-27, I-a-29, I-a-30, I-a-31, I-a-33, I-a-34, I-a-35, I-a-36, I-a-37, I-a-38, I-a-39, 1-a-40, I-a-41, I-a-42, I-a-43, I-a-44, I-a-45, I-a-46, I-a-47, I-a-48, I-a-49, I-a-50, I-a-51, I-a-52, I-a-53, I-a-54, I-a-55, I-a-57, I-a-58, I-a-59, I-a-60, I-a-61, I-a-62, I-a-63, I-a-64, I-a-65, 1-a-66, I-a-67, I-a-69, I-a-70, I-a-71, I-b-1, I-c-1, I-c-2, I-c-3

Example 5

*Tetranychus* Test, OP-Resistant (TETRUR Spray Treatment)

Solvent: 78.0 parts by weight of acetone
1.5 parts by weight of dimethylformamide
Emulsifier: 0.5 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

RPI 2008-65.doc

Discs of bean leaves (*Phaseolus vulgaris*) which are infested by all stages of the greenhouse red spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 100 g/ha, an effect of ≥80%:

Ex. No. I-a-3, I-a-4, I-a-5, I-a-2, I-a-10, I-a-11, I-a-15, I-a-12, I-a-13, I-a-19, I-a-18, I-a-26, I-a-22, I-a-23, I-a-27, I-a-30, I-a-31, I-a-35, I-a-36, I-a-38, I-a-39, I-a-40, I-a-41, I-a-43, I-a-44, I-a-47, I-a-51, I-a-52, I-a-53, I-a-60, I-a-61, I-a-68, I-a-71 I-b-1, I-c-1, I-c-2, I-c-3

Example 6

*Lucillia cuprina* Test (LUCICU)

Solvent: dimethyl sulphoxide

To prepare a suitable active compound preparation, 1 part by weight of active compound is mixed with the stated amount of solvent, and the concentrate is diluted with water to the desired concentration.

Vessels containing horse meat treated with the active compound preparation of the desired concentration are populated with *Lucilia cuprina* larvae.

After the desired period of time, the kill in % is determined. 100% means that all of the *larvae* have been killed; 0% means that none of the larvae have been killed.

In this test, for example, the following compounds of the Preparation Examples show, at an application rate of 100 ppm, an effect of ≥80%:

Ex. No. I-a-3

Example 7

*Boophilus microplus* Test (BOOPMI Injection)

Solvent: dimethyl sulphoxide

To prepare a suitable active compound preparation, 1 part by weight of active compound is mixed with the stated amount of solvent, and the concentrate is diluted with water to the desired concentration.

The solution of active compound is injected into the abdomen (*Boophilus microplus*), and the animals are transferred into dishes and kept in a climatised room. The activity is assessed by position of fertile eggs.

After the desired period of time, the effect in % is determined. 100% means that none of the ticks has laid any fertile eggs.

In this test, for example, the following compounds of the Preparation Examples show, at an application rate of 20 µg/animal, good efficacy: see table Ex. No. I-a-3, I-c-3

Example 8

*Heliothis virescens* Test—Treatment of Transgenic Plants

Solvent: 7 parts by weight of acetone
Emulsifier: 2 parts by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of a transgenic cultivar are treated by being sprayed with the preparation of active compound of the desired concentration and are populated with the tobacco budworm *Heliothis virescens* while the leaves are still moist.

After the desired period of time, the kill of the insects is determined.

Example 9

Critical Concentration Test/Soil Insects—Treatment of Transgenic Plants

Test insect: *Diabrotica balteata*—larvae in soil
Solvent: 7 parts by weight of acetone
Emulsifier: 1 parts by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually irrelevant, only the amount by weight of active compound per volume unit of soil, which is stated in ppm (mg/l) matters. The soil is filled into 0.25 l pots and these are allowed to stand at 20° C.

Immediately after the preparation, 5 pregerminated maize maizes of a transgenic cultivar are placed into each pot. After 2 days, the test insects in question are placed into the treated soil. After a further 7 days, the efficacy of the active compound is determined by counting the maize plants that have emerged (1 plant=20% efficacy).

The invention claimed is:

1. A compound of the formula (II)

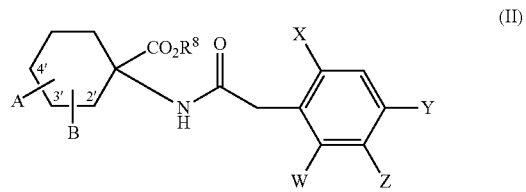

in which
W represents hydrogen, halogen, alkyl, alkenyl, alkynyl, optionally substituted cycloalkyl, alkoxy, alkenyloxy, haloalkyl, haloalkoxy or cyano,
X represents halogen, alkyl, alkenyl, alkynyl, optionally substituted cycloalkyl, alkoxy, alkenyloxy, alkylthio, alkylsulphinyl, alkylsulphonyl, haloalkyl, haloalkoxy, haloalkenyloxy, nitro or cyano,
Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl,
A represents alkoxy,
B represents alkyl, where
A and B are attached to the same carbon atom,
and
$R^8$ represents alkyl.

2. A compound of the formula (XIV)

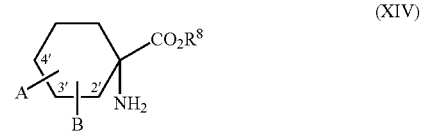

in which
A represents alkoxy,
B represents alkyl, where
A and B are attached to the same carbon atom,
and
$R^8$ represents alkyl.

3. A compound of the formula (XVI)

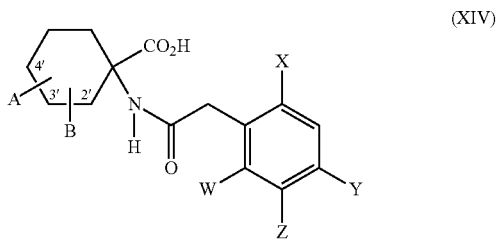

in which
W represents hydrogen, halogen, alkyl, alkenyl, alkynyl, optionally substituted cycloalkyl, alkoxy, alkenyloxy, haloalkyl, haloalkoxy or cyano, X represents halogen, alkyl, alkenyl, alkynyl, optionally substituted cycloalkyl, alkoxy, alkenyloxy, alkylthio, alkylsulphinyl, alkylsulphonyl, haloalkyl, haloalkoxy, haloalkenyloxy, nitro or cyano, Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl, A represents alkoxy, B represents alkyl, where A and B are attached to the same carbon atom.

4. A compound of the formula (XVII)

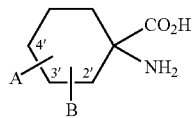

(XVII)

in which

A represents alkoxy,

B represents alkyl, where

A and B are attached to the same carbon atom.

5. A compound of the formula (XVIII)

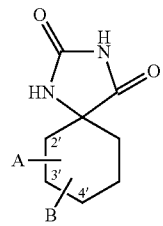

(XVIII)

in which

A represents alkoxy,

B represents alkyl, where

A and B are attached to the same carbon atom.

* * * * *